US011994520B2

(12) United States Patent
Hauser et al.

(10) Patent No.: US 11,994,520 B2
(45) Date of Patent: May 28, 2024

(54) DEVELOPING LATERAL FLOW IMMUNOCHROMATOGRAPHY (LFIA) PEPTIDE-BASED TEST STRIPS FOR RAPID DETECTION OF ANTIGENS AND ANTIBODIES AGAINST SPECIFIC ANTIGENS

(71) Applicant: KING ABDULLAH UNIVERSITY OF SCIENCE AND TECHNOLOGY, Thuwal (SA)

(72) Inventors: Charlotte A. E. Hauser, Thuwal (SA); Panagiotis Bilalis, Thuwal (SA); Dana Alhattab, Thuwal (SA); Hepi Hari Susapto, Thuwal (SA); Manola Moretti, Thuwal (SA); Salwa Alshehri, Thuwal (SA); Ali Aldoukhi, Thuwal (SA); Hamed Albalawi, Thuwal (SA); Hattan Boshah, Thuwal (SA); Abdulelah Alrashoudi, Thuwal (SA); Alexander Valle Perez, Thuwal (SA); Rosario Perez Pedroza, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 18/038,107

(22) PCT Filed: Nov. 22, 2021

(86) PCT No.: PCT/IB2021/060795
§ 371 (c)(1),
(2) Date: May 22, 2023

(87) PCT Pub. No.: WO2022/107089
PCT Pub. Date: May 27, 2022

(65) Prior Publication Data
US 2023/0408518 A1 Dec. 21, 2023

Related U.S. Application Data

(60) Provisional application No. 63/117,138, filed on Nov. 23, 2020.

(51) Int. Cl.
*C07K 14/005* (2006.01)
*C07K 14/08* (2006.01)
*G01N 33/543* (2006.01)
*G01N 33/549* (2006.01)
*G01N 33/558* (2006.01)
*G01N 33/569* (2006.01)

(52) U.S. Cl.
CPC ..... *G01N 33/56983* (2013.01); *C07K 14/005* (2013.01); *G01N 33/54388* (2021.08); *G01N 33/558* (2013.01); *C07K 2319/00* (2013.01); *G01N 2469/20* (2013.01)

(58) Field of Classification Search
CPC .............. C07K 14/005; C07K 2319/40; C07K 2319/00; C12N 2770/20022; G01N 2333/165
See application file for complete search history.

(56) References Cited

U.S. PATENT DOCUMENTS

| | | |
|---|---|---|
| 2003/0175410 A1 | 9/2003 | Campbell et al. |
| 2011/0008293 A1 | 1/2011 | Bhandari |
| 2014/0012225 A1 | 1/2014 | Yoo et al. |
| 2016/0288414 A1 | 10/2016 | Ozbolat et al. |
| 2017/0056548 A1 | 3/2017 | Lee et al. |
| 2018/0118978 A1 | 5/2018 | Yabu et al. |
| 2019/0219572 A1 | 7/2019 | Mehra et al. |

FOREIGN PATENT DOCUMENTS

| | | |
|---|---|---|
| CN | 105 881 908 A | 8/2016 |
| JP | 2013 009598 A | 1/2013 |
| KR | 2016 0091993 A | 8/2016 |
| KR | 10-2020-0007537 A | 1/2020 |
| KR | 10-2021-0104339 A | 8/2021 |
| WO | 2007/102735 A1 | 9/2007 |
| WO | 2014/197999 A1 | 12/2014 |
| WO | 2015/080671 A1 | 6/2015 |
| WO | 2017/089963 A1 | 6/2017 |
| WO | 2018/207037 A1 | 11/2018 |

OTHER PUBLICATIONS

Alrashoudi et al., "Fabrication of a Lateral Flow Assay for Rapid In-Field Detection of COVID-19 Antibodies Using Additive Manufacturing Printing Technologies", International Journal of Bioprinting, vol. 7, Issue 4, Article No. 399, pp. 76-84 (2021).
Farrera-Solar et al., "Identification of immunodominant linear epitopes from SARS-CoV2-patient plasma", PLoS ONE, vol. 15, Issue 9, e0238089, pp. 1-15 (2020).
Saatci, "Newly developed diagnostic methods for SARS-CoV-2 detection", Turkish Journal of Biochemistry, vol. 45, Issue 5, pp. 465-474 (2020).

(Continued)

*Primary Examiner* — Barry A Chestnut
(74) *Attorney, Agent, or Firm* — Ajay A. Jagtiani; Miles & Stockbridge P.C.

(57) ABSTRACT

The present disclosure relates a method of fabricating a literal flow immunoassay (LFIA) for the diagnosis of diseases, including COVID-19. The present disclosure further relates to a fusion-epitopes peptide that can be used in the LFIA test to improve sensitivity, specificity and accuracy of the test.

19 Claims, 18 Drawing Sheets

Specification includes a Sequence Listing.

(56) References Cited

OTHER PUBLICATIONS

Xiang et al., "A novel double antibody sandwich-lateral flow immunoassay for the rapid and simple detection of hepatitis C virus", International Journal of Molecular Medicine, vol. 30, pp. 1041-1047 (2012).

Search Report and Written Opinion received in PCT Application No. PCT/IB2021/060795 dated Mar. 18, 2022.

Grifoni, A.; Sidney, J.; Zhang, Y.; Scheuermann, R. H.; Peters, B.; Sette, A., A Sequence Homology and Bioinformatic Approach Can Predict Candidate Targets for Immune Responses to Sars-Cov-2. Cell Host Microbe. 2020, 27 (4), 671-680.e2.

Zhang, B.-z.; Hu, Y.-f.; Chen, L.-I.; Yau, T.; Tong, Y.-g.; Hu, J.-c.; Cai, J.-p.; Chan, K.-H.; Dou, Y.; Deng, J.; Wang, X.-I.; Hung, I. F.-N.; To, K. K.-W.; Yuen, K. Y.; Huang, J.-D., Mining of Epitopes on Spike Protein of Sars-Cov-2 from Covid-19 Patients. Cell Res. 2020, 30 (8), 702-704.

Ahmed, S. F.; Quadeer, A. A.; McKay, M. R., Covidep: A Web-Based Platform for Real-Time Reporting of Vaccine Target Recommendations for Sars-Cov-2. Nat. Protoc. 2020, 15 (7), 2141-2142.

Grossberg, A. N.; Koza, L. A.; Ledreux, A.; Prusmack, C.; Krishnamurthy, H. K.; Jayaraman, V.; Granholm, A.-C.; Linseman, D. A., A Multiplex Chemiluminescent Immunoassay for Serological Profiling of Covid-19-Positive Symptomatic and Asymptomatic Patients. Nat Commun. 2021, 12 (1), 740.

Diener, C.; Garza Ramos Martinez, G.; Moreno Blas, D.; Castillo González, D. A.; Corzo, G.; Castro-Obregon, S.; Del Rio, G., Effective Design of Multifunctional Peptides by Combining Compatible Functions. PLoS Comput. Biol. 2016, 12 (4), e1004786-e1004786.

Chen, Z.; Zhang, Z.; Zhai, X.; Li, Y.; Lin, L.; Zhao, H.; Bian, L.; Li, P.; Yu, L.; Wu, Y.; Lin, G., Rapid and Sensitive Detection of Anti-Sars-Cov-2 Igg, Using Lanthanide-Doped Nanoparticles-Based Lateral Flow Immunoassay. Anal. Chem. 2020, 92 (10), 7226-7231.

Lew, T. T. S.; Aung, K. M. M.; Ow, S. Y.; Amrun, S. N.; Sutarlie, L.; Ng, L. F. P.; Su, X., Epitope-Functionalized Gold Nanoparticles for Rapid and Selective Detection of Sars-Cov-2 Igg Antibodies. ACS Nano. 2021, 15 (7), 12286-12297.

Haberland, A.; Muller, J.; Wallukat, G.; Wenzel, K., Antigen-Free Control Wells in an Elisa Set-up for the Determination of Autoantibodies against G Protein-Coupled Receptors—a Requisite for Correct Data Evaluation. Anal. Bioanal. Chem. 2018, 410 (21), 5101-5105.

Ju, B.; Zhang, Q.; Ge, J.; Wang, R.; Sun, J.; Ge, X.; Yu, J.; Shan, S.; Zhou, B.; Song, S.; Tang, X.; Yu, J.; Lan, J.; Yuan, J.; Wang, H.; Zhao, J.; Zhang, S.; Wang, Y.; Shi, X.; Liu, L.; Zhao, J.; Wang, X.; Zhang, Z.; Zhang, L., Human Neutralizing Antibodies Elicited by Sars-Cov-2 Infection. Nature. 2020, 584 (7819), 115-119.

Kang, S.; Yang, M.; He, S.; Wang, Y.; Chen, X.; Chen, Y.-Q.; Hong, Z.; Liu, J.; Jiang, G.; Chen, Q.; Zhou, Z.; Zhou, Z.; Huang, Z.; Huang, X.; He, H.; Zheng, W.; Liao, H.-X.; Xiao, F.; Shan, H.; Chen, S., A Sars-Cov-2 Antibody Curbs Viral Nucleocapsid Protein-Induced Complement Hyperactivation. Nat Commun. 2021, 12 (1), 2697.

Norel, R.; Petrey, D.; Wolfson, H. J.; Nussinov, R., Examination of Shape Complementarity in Docking of Unbound Proteins. Proteins: Structure, Function, and Bioinformatics. 1999, 36 (3), 307-317.

Brenke, R.; Hall, D. R.; Chuang, G. Y.; Comeau, S. R.; Bohnuud, T.; Beglov, D.; Schueler-Furman, O.; Vajda, S.; Kozakov, D., Application of Asymmetric Statistical Potentials to Antibody-Protein Docking. Bioinformatics. 2012, 28 (20), 2608-14.

Desta, I. T.; Porter, K. A.; Xia, B.; Kozakov, D.; Vajda, S., Performance and Its Limits in Rigid Body Protein-Protein Docking. Structure. 2020, 28 (9), 1071-1081.e3.

Kozakov, D.; Beglov, D.; Bohnuud, T.; Mottarella, S. E.; Xia, B.; Hall, D. R.; Vajda, S., How Good Is Automated Protein Docking? Proteins. 2013, 81 (12), 2159-66.

Kozakov, D.; Hall, D. R.; Xia, B.; Porter, K. A.; Padhorny, D.; Yueh, C.; Beglov, D.; Vajda, S., The Cluspro Web Server for Protein-Protein Docking. Nat. Protoc. 2017, 12 (2), 255-278.

Vajda, S.; Yueh, C.; Beglov, D.; Bohnuud, T.; Mottarella, S. E.; Xia, B.; Hall, D. R.; Kozakov, D., New Additions to the Cluspro Server Motivated by Capri. Proteins. 2017, 85 (3), 435-444.

Gonzalez-Moa, M. J.; Van Dorst, B.; Lagatie, O.; Verheyen, A.; Stuyver, L.; Biamonte, M. A., Proof-of-Concept Rapid Diagnostic Test for Onchocerciasis: Exploring Peptide Biomarkers and the Use of Gold Nanoshells as Reporter Nanoparticles. ACS Infect Dis. 2018, 4 (6), 912-917.

Robin, X.; Turck, N.; Hainard, A.; Tiberti, N.; Lisacek, F.; Sanchez, J.-C.; Muller, M., Proc: An Open-Source Package for R and S+ to Analyze and Compare Roc Curves. BMC Bioinformatics. 2011, 12 (1), 77.

Youden, W. J., Index for Rating Diagnostic Tests. Cancer. 1950, 3 (1), 32-35.

Guan WJ, Ni ZY, Hu Y, et al., 2020, Clinical Characteristics of Coronavirus Disease 2019 in China. N. Engl. J. Med., 382:1708-20.

Chan JF, Kok KH, Zhu Z, et al., 2020, Genomic Characterization of the 2019 Novel Human-pathogenic Coronavirus Isolated from a Patient with Atypical Pneumonia after Visiting Wuhan. Emerg Microbes Infect, 9:221-36.

Huang C, Wang Y, Li X, et al., 2020, Clinical Features of Patients Infected with 2019 Novel Coronavirus in Wuhan, China. Lancet, 395:497-506.

Cucinotta D, Vanelli M, 2020, WHO Declares COVID-19 a Pandemic. Acta Biomed, 91:157-60.

Zou L, Ruan F, Huang M, et al., 2020, SARS-CoV-2 Viral Load in Upper Respiratory Specimens of Infected Patients. N Engl J Med, 382:1177-9.

To KK, Tsang OT, Leung WS, et al., 2020, Temporal Profiles of Viral Load in Posterior Oropharyngeal Saliva Samples and Serum Antibody Responses during Infection by SARSCoV-2: An Observational Cohort Study. Lancet Infect Dis, 20:565-74.

Winter AK, Hegde ST, 2020, The Important Role of Serology for COVID-19 Control. Lancet Infect Dis, 20:758-59.

Dan JM, Mateus J, Kato Y, et al., 2021, Immunological Memory to SARS-CoV-2 Assessed for up to 8 Months after Infection. Science, 371:eabf4063.

Martin J, Tena N, Asuero AG, 2021, Current State of Diagnostic, Screening and Surveillance Testing Methods for COVID-19 from an Analytical Chemistry Point of View. Microchem J, 167:106305.

Schuler CF, Gherasim C, O'Shea K, et al., 2021, Accurate Point-of-care Serology Tests for COVID-19. PLoS One, 16:e0248729.

Banerjee R, Jaiswal A, 2018, Recent Advances in Nanoparticle-based Lateral Flow Immunoassay as a Pointof-care Diagnostic Tool for Infectious Agents and Diseases. Analyst, 143:1970-96.

Adams E, Ainsworth M, Anand R, et al., 2020, Antibody Testing for COVID-19: A Report from the National COVID Scientific Advisory Panel. Wellcome Open Res, 5:139.

Dinnes J, Deeks JJ, Berhane S, et al., 2021, Rapid, Pointof-care Antigen and Molecular-based Tests for Diagnosis of SARS-CoV-2 Infection. Cochrane Database Syst Rev, 3:CD013705.

Ozbolat IT, Hospodiuk M, 2016, Current Advances and Future Perspectives in Extrusion-based Bioprinting. Biomaterials, 76:321-43.

Eckelman MJ, Sherman JD, 2018, Estimated Global Disease Burden From US Health Care Sector Greenhouse Gas Emissions. Am J Public Health, 108:S120-2.

Leiden A, Cerdas F, Noriega D, et al., 2020, Life Cycle Assessment of a Disposable and a Reusable Surgery Instrument Set for Spinal Fusion Surgeries. Resour Conserv Recycl, 156:104704.

Unger SR, Hottle TA, Hobbs SR, et al., 2017, Do Single use Medical Devices Containing Biopolymers Reduce the Environmental Impacts of Surgical Procedures Compared with their Plastic Equivalents? J Health Serv Res Policy, 22:218-25.

Gebhardt A, 2011, Understanding Additive Manufacturing. In: Understanding Additive Manufacturing. Hanser Pub Inc., Cincinnati, OH.

Joshi SC, Sheikh AA, 2015, 3D Printing in Aerospace and its Long-term Sustainability. Virtual Phys Prototyp, 10:175-85.

(56) References Cited

OTHER PUBLICATIONS

Ng WL, Chua CK, Shen YF, 2019, Print Me an Organ! Why We Are Not There Yet. Prog Polym Sci, 97:101145.

Pant A, Lee AY, Karyappa R, et al., 2021, 3D Food Printing of Fresh Vegetables Using Food Hydrocolloids for Dysphagic Patients. Food Hydrocolloids, 114:106546.

Choong YY, Tan HW, Patel DC, et al., 2020, The Global Rise of 3D Printing during the COVID-19 Pandemic. Nat Rev Mater, 5:637-9.

Harvey WT, Carabelli AM, Jackson B, et al., 2021, SARSCoV- 2 Variants, Spike Mutations and Immune Escape. Nat Rev Microbiol, 19:409-24.

World Health Organization, 2021, Tracking SARS-CoV-2 Variants, World Health Organization, Geneva. [Last accessed on Jul. 25, 2021].

Jazayeri MH, Amani H, Pourfatollah AA, et al., 2016, Enhanced Detection Sensitivity of Prostate-specific Antigen via PSA-Conjugated Gold Nanoparticles Based on Localized Surface Plasmon Resonance: GNP-coated Anti-PSA/LSPR as a Novel Approach for the Identification of Prostate Anomalies. Cancer Gene Ther, 23:365-9.

Pollitt MJ, Buckton G, Piper R, et al., 2015, Measuring Antibody Coatings on Gold Nanoparticles by Optical Spectroscopy. RSC Adv, 5:24521-7.

Yetisen AK, Akram MS, Lowe CR, 2013, Paper-based Microfluidic Point-of-care Diagnostic Devices. Lab Chip, 13:2210-51.

Stansbury JW, Idacavage MJ, 2016, 3D Printing with Polymers: Challenges among Expanding Options and Opportunities. Dent Mater, 32:54-64.

Infuehr R, Pucher N, Heller C, et al., 2007, Functional Polymers by Two-photon 3D Lithography. Appl Surface Sci, 254:836-40.

Milovanović A, Milošević M, Mladenović G, et al., 2019, Experimental Dimensional Accuracy Analysis of Reformer Prototype Model Produced by FDM and SLA 3D Printing Technology. Springer International Publishing, Cham, p. 84-95.

Gibson I, Rosen D, Stucker B, et al., 2021, Material Extrusion. In: Additive Manufacturing Technologies. Springer International Publishing, Cham, p. 171-201.

Kun K, 2016, Reconstruction and Development of a 3D Printer Using FDM Technology. Proc Eng, 149:203-211.

Gibson I, Rosen D, Stucker B, 2015, Vat Photopolymerization Processes. In: Additive Manufacturing Technologies: 3D Printing, Rapid Prototyping, and Direct Digital Manufacturing. Springer New York, p. 63-106.

Cui, J.; Li, F.; Shi, Z. L., Origin and Evolution of Pathogenic Coronaviruses. Nat. Rev. Microbiol. 2019, 17 (3), 181-192.

Venter, M.; Richter, K., Towards Effective Diagnostic Assays for Covid-19: A Review. J. Clin. Pathol. 2020, 73 (7), 370-377.

Deeks, J. J.; Dinnes, J.; Takwoingi, Y.; Davenport, C.; Spijker, R.; Taylor-Phillips, S.; Adriano, A.; Beese, S.; Dretzke, J.; Ferrante di Ruffano, L.; Harris, I. M.; Price, M. J.; Dittrich, S.; Emperador, D.; Hooft, L.; Leeflang, M. M.; Van den Bruel, A., Antibody Tests for Identification of Current and Past Infection with Sars-Cov-2. Cochrane Database Syst. Rev. 2020, 6 (6), Cd013652.

Kohl, T. O.; Ascoli, C. A., Indirect Immunometric Elisa. Cold Spring Harb Protoc. 2017, 2017 (5).

Mishra, A. R.; Hutke, V. R.; Satav, A. R.; Ali, S. A.; Daginawala, H. F.; Singh, L. R.; Kashyap, R. S., Synthetic Peptides Are Better Than Native Antigens for Development of Elisa Assay for Diagnosis of Tuberculosis. Int. J. Pept. Res. Ther. 2017, 23 (2), 247-257.

Petherick, A., Developing Antibody Tests for Sars-Cov-2. Lancet. 2020, 395 (10230), 1101-1102.

Groß, A.; Hashimoto, C.; Sticht, H.; Eichler, J., Synthetic Peptides as Protein Mimics. Front. Bioeng. Biotechnol. 2016, 3 (211).

Poh, C. M.; Carissimo, G.; Wang, B.; Amrun, S. N.; Lee, C. Y.; Chee, R. S.; Fong, S. W.; Yeo, N. K.; Lee, W. H.; Torres-Ruesta, A.; Leo, Y. S.; Chen, M. I.; Tan, S. Y.; Chai, L. Y. A.; Kalimuddin, S.; Kheng, S. S. G.; Thien, S. Y.; Young, B. E.; Lye, D. C.; Hanson, B. J.; Wang, C. I.; Renia, L.; Ng, L. F. P., Two Linear Epitopes on the Sars-Cov-2 Spike Protein That Elicit Neutralising Antibodies in Covid-19 Patients. Nat Commun. 2020, 11 (1), 2806.

Alves, D.; Curvello, R.; Henderson, E.; Kesarwani, V.; Walker, J. A.; Leguizamon, S. C.; McLiesh, H.; Raghuwanshi, V. S.; Samadian, H.; Wood, E. M.; McQuilten, Z. K.; Graham, M.; Wieringa, M.; Korman, T. M.; Scott, T. F.; Banaszak Holl, M. M.; Garnier, G.; Corrie, S. R., Rapid Gel Card Agglutination Assays for Serological Analysis Following Sars-Cov-2 Infection in Humans. ACS Sensors. 2020, 5 (8), 2596-2603.

Amrun, S. N.; Lee, C. Y.; Lee, B.; Fong, S. W.; Young, B. E.; Chee, R. S.; Yeo, N. K.; Torres-Ruesta, A.; Carissimo, G.; Poh, C. M.; Chang, Z. W.; Tay, M. Z.; Chan, Y. H.; Chen, M. I.; Low, J. G.; Tambyah, P. A.; Kalimuddin, S.; Pada, S.; Tan, S. Y.; Sun, L. J.; Leo, Y. S.; Lye, D. C.; Renia, L.; Ng, L. F. P., Linear B-Cell Epitopes in the Spike and Nucleocapsid Proteins as Markers of Sars-Cov-2 Exposure and Disease Severity. EBioMedicine. 2020, 58, 102911.

Farrera-Soler, L.; Daguer, J. P.; Barluenga, S.; Vadas, O.; Cohen, P.; Pagano, S.; Yerly, S.; Kaiser, L.; Vuilleumier, N.; Winssinger, N., Identification of Immunodominant Linear Epitopes from Sars-Cov-2 Patient Plasma. PLoS One. 2020, 15 (9), e0238089.

Li, Y.; Lai, D. Y.; Lei, Q.; Xu, Z. W.; Wang, F.; Hou, H.; Chen, L.; Wu, J.; Ren, Y.; Ma, M. L.; Zhang, B.; Chen, H.; Yu, C.; Xue, J. B.; Zheng, Y. X.; Wang, X. N.; Jiang, H. W.; Zhang, H. N.; Qi, H.; Guo, S. J.; Zhang, Y.; Lin, X.; Yao, Z.; Pang, P.; Shi, D.; Wang, W.; Yang, X.; Zhou, J.; Sheng, H.; Sun, Z.; Shan, H.; Fan, X.; Tao, S. C., Systematic Evaluation of Igg Responses to Sars-Cov-2 Spike Protein-Derived Peptides for Monitoring Covid-19 Patients. Cell. Mol. Immunol. 2021, 18 (3), 621-631.

Polvere, I.; Voccola, S.; Cardinale, G.; Fumi, M.; Aquila, F.; Parrella, A.; Madera, J. R.; Stilo, R.; Vito, P.; Zotti, T., A Peptide-Based Assay Discriminates Individual Antibody Response to Sars-Cov-2. Genes Dis. 2021.

Simula, E. R.; Manca, M. A.; Jasemi, S.; Uzzau, S.; Rubino, S.; Manchia, P.; Bitti, A.; Palermo, M.; Sechi, L. A., Hcov-NI63 and Sars-Cov-2 Share Recognized Epitopes by the Humoral Response in Sera of People Collected Pre- and During Cov-2 Pandemic. Microorganisms. 2020, 8 (12).

Li, Y.; Lai, D.-y.; Zhang, H.-n.; Jiang, H.-w.; Tian, X.; Ma, M.-l.; Qi, H.; Meng, Q.-f.; Guo, S.-j.; Wu, Y.; Wang, W.; Yang, X.; Shi, D.-w.; Dai, J.-b.; Ying, T.; Zhou, J.; Tao, S.-c., Linear Epitopes of Sars-Cov-2 Spike Protein Elicit Neutralizing Antibodies in Covid-19 Patients. Cell. Mol. Immunol. 2020, 17 (10), 1095-1097.

Ernst, E.; Wolfe, P.; Stahura, C.; Edwards, K. A., Technical Considerations to Development of Serological Tests for Sars-Cov-2. Talanta. 2021, 224, 121883-121883.

Ayouba, A.; Touré, A.; Butel, C.; Keita, A. K.; Binetruy, F.; Sow, M. S.; Foulongne, V.; Delaporte, E.; Peeters, M., Development of a Sensitive and Specific Serological Assay Based on Luminex Technology for Detection of Antibodies to Zaire Ebola Virus. J. Clin. Microbiol. 2017, 55 (1), 165-176.

Zhang et al., "Catechol functionalized hyperbranched polymers as biomedical materials", Polymers in Polymer Science, vol. 78, pp. 47-55 (2018).

Examination Report received in Saudi Arabian Application No. 523442624 dated Sep. 28, 2023.

International Search Report and Written Opinion received in PCT Application No. PCT/IB2023/056328 dated Oct. 13, 2023.

Written Opinion received in Singapore Application No. 10202112455P dated Jul. 11, 2023.

Office Action received in Japanese Application No. 2019-561848 dated May 22, 2023.

Notice of Final Rejection received in Korean Application No. 10-2019-7036272 dated May 25, 2023.

European Search Report received in European Application No. 23159765.9 dated Jun. 22, 2023.

Ali et al., "A Non-Canonical NRPS Is Involved in the Synthesis of Fungisporin and Related Hydrophobic Cyclic Tetrapeptides in Penicillium chrysogenum", PLOS ONE; vol. 9, Issue 6, e98212 (2014).

Pubchem CID: 93078 "L-Aspartyl-L_phenylalanine" (2005).

Vasco et al., "Macrocyclization of Peptide Side Chains by the Ugi Reaction: Achieving Peptide Folding and Exocyclic N-Functionalization in One Shot", The Journal of Organic Chemistry, 80, pp. 6697-6707 (2015).

Viral epitope profiling of Covid-19 patients reveals cross-reactivity and corelates of severity shrock, E., Fujimura, E., Kula, T., Timms,

(56) References Cited

OTHER PUBLICATIONS

R., Lee, I., Leng, Y., Robinson,M., Sie,B.,Li,M.,Chen,L.,Logue,J. Zuiani,A.,McCulloch,D.,Lelis,F.,Henson,S.,Monaco,D.,Travers,M. Habibi,S.,Clark Trocha,A.,Li,J.,Hatri,A.,Chu,H.,Villani,A.,Kays,K. Godber,M.,Hacohen,N.Filbin,M.Yu,F.Walker,B.,Wesemann,D. Larma, B.,Lederer,J.,Elledge,S. (Science,2020,370:1-15).

Paired heavy and light chain signatures contribute to potent SARS-CoV-2 neutralization in public antibody responses Banach,B. Cerutti, G.,Fahad,A.,Shen,C.,Oliveira de Souza,M.,Katsamba, P.,Tsybovsky,Y.,Wang,P.,Nair,M.,Huang,Y.,Urdaniz,I.,Steiner, P.,Gutierrez-Gonzalez,M.,Liu,L.,Acevedo,S.,Nazzari,A.,Wolfe,J.,Luo, Y.,Olia, A.,Teng,I.,Yu,J.,Zhou,T.,Reddem,E.,Bimela,J.,Pan,X.,Madan, B.,Laflin,A.,Nimrania,R.,Yuen,K.,Whitehead,T.,Ho,D.,Kwong, P.,Shapiro,L.,DeKosky,B. (bioRxiv reprint;2020:1-58).

RCSB Protein Data Bank: powerful new tools for exploring 3D structures of biological macromolecules for basic and applied research and education in:fundamental biology, biomedicine,biotechnology,bioengineering and energy sciences Burley, S.,Bhikadiya,C.,Bi,C.,Bittrich,S.,Chen,L.,Crichlow,G.,Christine, C.,Dalenberg,K.,Costanzo,L.,Duarte,J.,Dutta,S.,Feng,Z.,Ganesan, S.,Goodsell,D.,Ghosh,S.,Green,R.,Guranovic,V.,Guzenko, D.,Hudson, B.,Lawson,C.,Liang,Y.,Lowe,R.,Namkoong,H.,Peisach,E. Persikova,I., Randle,C.,Rose,A.,Rose,Y.,Sali,A.,Segura, J.,Sekharan, M.,Shao,C.,Tao,Y.,Voigt,M.,Westbrook,J.,Young,J.,Zardecki, C.,Zhuravleva,M. (Nucleic Acids Research, 2021,49:D437-D451).

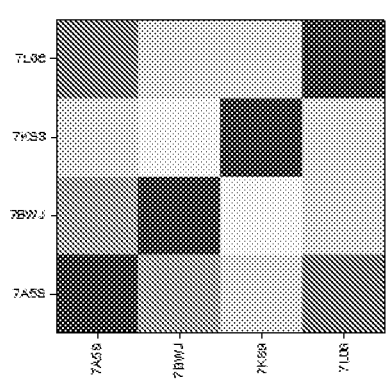 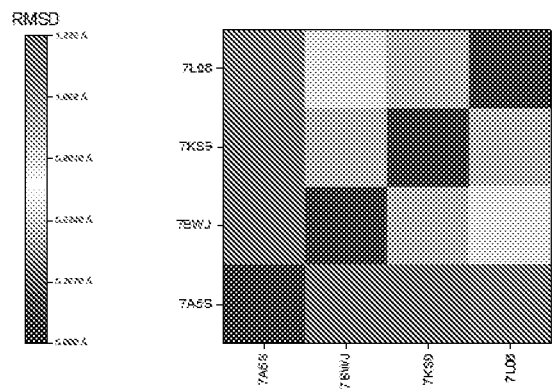
FIG. 24  FIG. 25
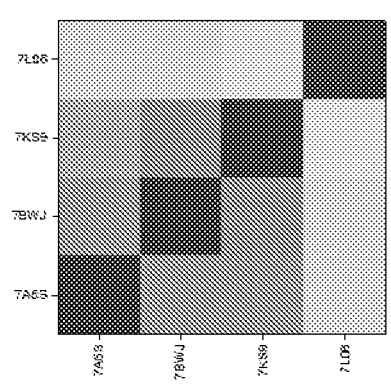 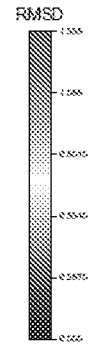
FIG. 26
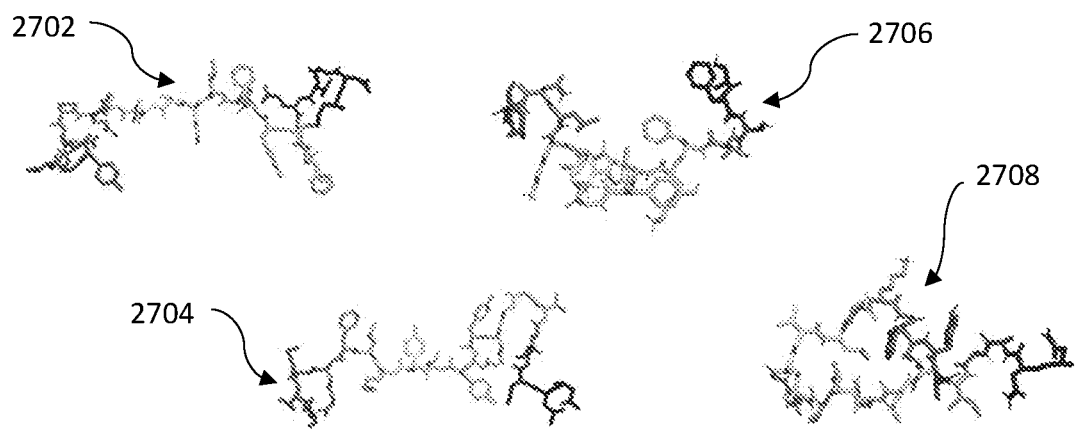
FIG. 27

SEQUENCE LISTING

```
<160> NUMBER OF SEQ ID NOS: 19

<210> SEQ ID NO 1
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin

<400> SEQUENCE: 1

Lys Cys Asn Gly Val Glu Gly Phe Asn Cys Tyr Phe Pro Leu Gln Ser
1               5                   10                  15

Tyr Gly Phe Gln Pro Thr Asn Gly Val Gly Tyr
            20                  25

<210> SEQ ID NO 2
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin

<400> SEQUENCE: 2

Lys Asn Leu Asp Ser Lys Val Gly Gly Asn Tyr Asn Tyr Leu Tyr Arg
1               5                   10                  15

Leu Phe Arg Lys Ser Asn
            20

<210> SEQ ID NO 3
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin

<400> SEQUENCE: 3

Lys Val Leu Leu Pro Leu Val Ser Ser Gln Cys Val Asn Leu Thr Thr
1               5                   10                  15

Arg Thr Gln Leu Pro Pro Ala Tyr Thr Asn
            20                  25

<210> SEQ ID NO 4
<211> LENGTH: 19
<212> TYPE: PRT
<213> ORGANISM: Artificial Sequence
<220> FEATURE:
<223> OTHER INFORMATION: Synthetic
<220> FEATURE:
```

```
<221> NAME/KEY: MOD_RES
<222> LOCATION: (1)..(1)
<223> OTHER INFORMATION: Biotin

<400> SEQUENCE: 4

Lys Ser Phe Ser Thr Phe Lys Cys Tyr Gly Val Ser Pro Thr Lys Leu
1               5                   10                  15

Asn Asp Leu

<210> SEQ ID NO 5
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin

<400> SEQUENCE: 5

Lys Gly Thr Gly Val Leu Thr Glu Ser Asn Lys Lys Phe Leu Pro Phe
1               5                   10                  15

Gln Gln Phe Gly Arg Asp Ile Ala
            20

<210> SEQ ID NO 6
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin

<400> SEQUENCE: 6

Lys Thr Gln Leu Asn Arg Ala Leu Thr Gly Ile Ala Val Glu Gln Asp
1               5                   10                  15

Lys Asn Thr Gln Glu Val Phe Ala Gln Val Lys
            20                  25

<210> SEQ ID NO 7
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin

<400> SEQUENCE: 7

Lys Phe Ser Gln Ile Leu Pro Asp Pro Ser Lys Pro Ser Lys Arg Ser
1               5                   10                  15

Phe Ile Glu Asp Leu Leu Phe Asn Lys Val
            20                  25

<210> SEQ ID NO 8
<211> LENGTH: 22
<212> TYPE: PRT
<213> ORGANISM: Artificial Sequence
<220> FEATURE:
<223> OTHER INFORMATION: Synthetic
<220> FEATURE:
```

```
<221> NAME/KEY: MOD_RES
<222> LOCATION: (1)..(1)
<223> OTHER INFORMATION: Biotin

<400> SEQUENCE: 8

Lys Asn Asn Ala Ala Ile Val Leu Gln Leu Pro Gln Gly Thr Thr Leu
1               5                   10                  15

Pro Lys Gly Phe Tyr Ala
            20

<210> SEQ ID NO 9
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin

<400> SEQUENCE: 9

Lys Asn Thr Gln Glu Val Phe Ala Gln Val Lys Gln Ile Tyr Lys Thr
1               5                   10                  15

Pro Pro Ile Lys Asp Phe Gly Gly Phe Asn Phe
            20                  25

<210> SEQ ID NO 10
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin

<400> SEQUENCE: 10

Lys Lys Thr Phe Pro Pro Thr Glu Pro Lys Lys Asp Lys Lys Lys Lys
1               5                   10                  15

Ala Asp Glu Thr Gln Ala Leu Pro Gln Arg Gln
            20                  25

<210> SEQ ID NO 11
<211> LENGTH: 55
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin

<400> SEQUENCE: 11

Lys Lys Thr Phe Pro Pro Thr Glu Pro Lys Lys Asp Lys Lys Lys Lys
1               5                   10                  15

Ala Asp Glu Thr Gln Ala Leu Pro Gln Arg Gln Ser Gly Ser Gly Ser
            20                  25                  30

Gly Thr Gly Val Leu Thr Glu Ser Asn Lys Lys Phe Leu Pro Phe Gln
        35                  40                  45

Gln Phe Gly Arg Asp Ile Ala
    50                  55
```

```
<210> SEQ ID NO 12
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin

<400> SEQUENCE: 12

Lys Cys Asn Gly Val Glu Gly Phe Asn Cys Tyr Phe Pro Leu Gln Ser
1               5                   10                  15

Tyr Gly Phe Gln Pro Thr Tyr Gly Val Gly Tyr
            20                  25

<210> SEQ ID NO 13
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin

<400> SEQUENCE: 13

Lys Gly Thr Gly Val Leu Thr Glu Ser Asn Lys Lys Phe Leu Pro Phe
1               5                   10                  15

Gln Gln Phe Gly Arg Asp Ile Asp
            20

<210> SEQ ID NO 14
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin

<400> SEQUENCE: 14

Lys Cys Asn Gly Val Lys Gly Phe Asn Cys Tyr Phe Pro Leu Gln Ser
1               5                   10                  15

Tyr Gly Phe Gln Pro Thr Asn Gly Val Gly Tyr
            20                  25

<210> SEQ ID NO 15
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin

<400> SEQUENCE: 15

Lys Val Leu Leu Pro Leu Val Ser Ser Gln Cys Val Asn Phe Thr Thr
1               5                   10                  15

Arg Thr Gln Leu Pro Pro Ala Tyr Thr Asn
            20                  25
```

<210> SEQ ID NO 16
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin

<400> SEQUENCE: 16

Lys Val Leu Leu Pro Leu Val Ser Ser Gln Cys Val Asn Leu Thr Asn
1               5                   10                  15

Arg Thr Gln Leu Pro Pro Ala Tyr Thr Asn
            20                  25

<210> SEQ ID NO 17
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin

<400> SEQUENCE: 17

Lys Val Leu Leu Pro Leu Val Ser Ser Gln Cys Val Asn Leu Thr Thr
1               5                   10                  15

Arg Thr Gln Leu Pro Ser Ala Tyr Thr Asn
            20                  25

<210> SEQ ID NO 18
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin

<400> SEQUENCE: 18

Lys Asn Leu Asp Ser Lys Val Gly Gly Asn Tyr Asn Tyr Arg Tyr Arg
1               5                   10                  15

Leu Phe Arg Lys Ser Asn
            20

<210> SEQ ID NO 19
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Biotin -continued

```
<400> SEQUENCE: 19

Lys Lys Thr Phe Pro Pro Thr Glu Pro Lys Lys Asp Lys Lys Lys Lys
1               5                   10                  15

Ala Tyr Glu Thr Gln Ala Leu Pro Gln Arg Gln
            20                  25
```

DEVELOPING LATERAL FLOW IMMUNOCHROMATOGRAPHY (LFIA) PEPTIDE-BASED TEST STRIPS FOR RAPID DETECTION OF ANTIGENS AND ANTIBODIES AGAINST SPECIFIC ANTIGENS

REFERENCE TO A "SEQUENCE LISTING"

This application is a 371 application of PCT Application No. PCT/IB2021/060795, entitled, "DEVELOPING LATERAL FLOW IMMUNOCHROMATOGRAPHY (LFIA) PEPTIDE-BASED TEST STRIPS FOR RAPID DETECTION OF ANTIGENS AND ANTIBODIES AGAINST SPECIFIC ANTIGENS", which has an international filing date of Nov. 22, 2021, which claims benefit of priority of U.S. Provisional Patent Application No. 63/117,138 entitled, "DEVELOPING LATERAL FLOW IMMUNOCHROMATOGRAPHY (LFIA) PEPTIDE-BASED TEST STRIPS FOR RAPID DETECTION OF SARS-COV-2 AND ANTI-SARS-COV-2 ANTIBODIES" filed Nov. 23, 2020. The entire contents and disclosures of these patent applications are incorporated herein by reference in their entirety.

BACKGROUND

Field of the Invention

The present disclosure relates a method of fabricating a literal flow immunoassay (LFIA) for the diagnosis of diseases, including COVID-19. The present disclosure further relates to a fusion-epitopes peptide that can be used in the LFIA test to improve sensitivity, specificity and accuracy of the test.

Background of the Invention

Severe acute respiratory syndrome coronavirus 2 (SARS-CoV-2) is the causative virus of coronavirus disease 2019 (COVID-19), and the first case was reported in China in December 2019[1]. SARS-CoV-2 is a RNA virus that belongs to the coronavirus family and has multiple structural proteins on its surface, including spike, nucleocapsid, membrane, and envelope proteins[2]. The virus causes severe respiratory symptoms requiring mechanical ventilation and intensive care unit admission, and contributes to high mortality rates. Moreover, the virus had high transmissibility between humans, and for that, the World Health Organization declared COVID-19 as a pandemic on Mar. 11, 2020[4]. Since then, huge efforts to identify people with active infection of SARS-CoV-2 were implemented in order to stop the spread of the virus. Detecting individuals with active infection require polymerase chain reaction testing in nasal or throat swab samples, and the test results are used to identify and isolate positive cases so as to limit the transmission of the virus[5]. Antibodies against the viral spike and nucleocapsid surface proteins are developed and can be detected in the serum of infected 14 days after the infection[6]. Thus, testing serum or blood samples for antibodies against the viral surface proteins, especially IgG, would provide information about people who had a history of prior infection and have recovered from the disease[6]. Therefore, antibody testing has an important role in epidemiological assessment of community spread of the virus and to guide policymakers when designing and introducing protective measures[7].

A recent study by Dan et al. reported that people who recovered from COVID-19 have immunity lasting for 6-8 months after the infection in which IgG antibodies could be detected by serology testing[8]. Screening for COVID-19 antibodies could provide valuable information about the level of immunity in the community. The screening can also be an important part in identifying who is immune and who is not when a majority of people return to work and transition to the new normal[7]. Furthermore, the detection of antibodies against SARS-CoV-2 can be used as a tool to monitor immunity against SARS-CoV-2 acquired through vaccines, which can be done using laboratory-based immunoassays such as chemiluminescence and enzyme-linked immunosorbent assay, or rapid tests such as lateral flow immunoassay (LFIA)[9]. Indeed, a cost-effective diagnostic tool would be beneficial for wide community screening. Rapid tests offer comparable outcomes to the laboratory-based tests and can be used when there is a need to identify people with immunity against the virus within a few minutes while having the advantages of being user-friendly, portable, and not requiring expensive instruments[10].

A LFIA is a point-of-care diagnostic device that offers a rapid and inexpensive test that targets analytes in the samples by providing qualitative or semi-quantitative results[11]. It consists of four essential parts, namely, the sample pad, conjugate pad, nitrocellulose membrane, and the absorption pad, which are assembled and placed in a housing cassette. One of the most predominant advantages of LFIA is the simplicity of the device as it can be used in the field without the need for any special equipment or sample processing. Moreover, since the beginning of the COVID-19 pandemic, there has been a tremendous effort to develop LFIA that can be used to detect viral antigens or serum antibodies for the identification of infected individuals or immune individuals, respectively[12,13]. As more research is being conducted to optimize and develop more accurate tests, there is a need for a rapid method to prototype and construct these LFIA.

Technologies such as three-dimensional (3D) printing and bioprinting can be used as tools to aid in the development of LFIA where time is of the essence such as global pandemic[14].

Another component of the LFIA is the cassette used to house and protect the testing strip from damage. Since the LFIA test can be used to detect different types of analytes, billions of LFIA tests and cassettes are manufactured annually[11]. Recently, there has been an increase in awareness regarding the environmental impact of medical devices, especially disposable devices[15-17]. Thus, the environmental impact should be taken into consideration when designing medical devices to limit this negative impact[16]. Since the LFIA cassette is made of polymers, it would be beneficial to consider how it can be designed in a way to decrease its environmental impact. Furthermore, using computer simulation for the 3D design, these iterations could be tested before the fabrication process. Furthermore, the simulation could be utilized to design and 3D print cassette with minimum polymeric material using different technologies.

In the past two decades, 3D printing technologies have been developed as essential prototyping techniques, industrially known as additive manufacturing technology, which are used as the primary prototyping technology in many applications today[18]. 3D printing provides an accessible method for fabrication of a customized design solution in a rapid controlled manner. Due to its high utility, it has developed tremendously in many fields, from aeronautics to sustainability, as well as medicine[19-21].

During the pandemic, there has been a massive increase in the innovations and application of 3D printing technologies. 3D printing technologies offered a wide range of on-demand solutions during a time where supply chains were constrained. Some of the applications of 3D printing during COVID-19 pandemic include the production of medical devices, personal protective equipment, and other devices that aid in controlling the spread of the virus[22]. With the evolutionary mutations of SARS-CoV-2 virus, we are facing new variants such as Delta variant[23,24]. Since the virus is changing at a fast pace, we need to utilize technologies that allow us to adapt to these changes and provide rapid solutions to protect our community.

The advantage of using 3D printing over the traditional methods, such as laser cutting, is that 3D printing offers a prototyping method to test multiple designs in short period of time. In addition, ease of accessibility to 3D printers makes them suitable for prototyping in a laboratory setting. Once the design is tested and finalized using 3D printing technology, it can be sent out for mass production.

In addition to the design and manufacturing of diagnostic tool, the selection of antigen to detect is also crucial for the accuracy and efficiency of diagnosis. The main antigenic part of the virus is the spike protein, a surface protein that facilitates viral entry into cells mainly through its interaction with Angiotensin-Converting Enzyme (ACE2) receptor.[34] The virus can be detected at the early stages of the disease by a Polymerase Chain Reaction (PCR) test from the first day of the infection until approximately 21 days after the infection.[6] Early detection of the virus is a crucial step to isolate cases and limit the virus spread.[5] Antibodies against the viral surface proteins, including the spike and nucleocapsid proteins, play an essential role in the immune system fight mechanism and detection of immunized individuals.[6] IgG and IgM antibodies start to appear seven days after the disease onset, and their level can be sustained in the blood for several months providing immunity against a second infection.[6] Therefore, detection of Covid-19 antibodies with a robust serological test with high sensitivity and specificity is needed to help contain and manage the pandemic.[35]

Serum antibodies are detected in clinical laboratories either using an enzyme-linked immunosorbent assay (ELISA) or a chemiluminescence immunoassay (CLIA).[36] In ELISA, the antigen of interest, protein or peptide, is attached to a microtiter plate and used to detect antibodies in the samples that bind to the antigen.[37] Peptide antigens have several advantages compared to protein antigens. First, peptides were reported to have better sensitivity and specificity when compared to proteins.[38] Second, producing proteins in their native form is challenging, which could negatively influence the consistency and outcomes of the test.[39] Lastly, peptides sequences can be readily changed to adapt any specific design requirements or change of viral protein sequence due to mutations in comparison to recombinant proteins.[40]

Several studies have reported peptide epitopes from the SARS-CoV-2 surface proteins that can recognize serum antibodies from Covid-19 patients.[41-47] Various peptide sequences were identified in different studies and were found to have different sensitivity, specificity, and accuracy of antibody detection.[41-47] For example, Poh et al. screened overlapping peptide epitopes from the whole spike protein using ELISA to identify epitopes with reactivity against SARS-CoV-2 antibodies.[41] They found two epitopes from the spike protein sequence (residues 553-570 and 809-826) that elicited a high response against Covid-19 antibodies. Li et al.[48] screened peptide epitopes spanning the entire length of the spike protein using microarray analysis and found similar epitopes to Poh et al.41 in addition to other epitopes that can be used to detect SARS-CoV-2 antibodies. Moreover, even though some common peptide sequences were identified, the diagnostic performance for these sequences varied among the studies.[41,48]

A recent study assessed antibodies response from different patients to several peptide epitopes using ELISA.[46] They found that antibodies from Covid-19 convalescents respond differently for each peptide; antibodies from some serum samples were detected by one peptide, while a different set of peptides detected antibodies from other samples. Thus, suggesting that a single peptide sequence might not be capable of detecting all patients with positive Covid-19 antibodies. One proposed way to resolve this issue is to use a pool or mixture of peptides when coating the microtiter plate to improve the sensitivity and specificity for detecting SARS-CoV-2 antibodies.[43, 45, 46]

Serological assays need to be highly sensitive and specific to detect the desired antibodies without false-negative or false-positive results. Therefore, several aspects need to be considered when developing a serological assay, including antigen selection.[49] Combining results from viral antigens have been shown to improve sensitivity and specificity for antibodies detection.[50] An alternative way to combine results from two antigens would be to synthesize one antigen with fused sequences from two different antigenic sites. This could result in less complexity when developing an immunoassay.

Therefore, there is a need for peptide antigens that can improve the sensitivity, specificity and accuracy for serological assays. Moreover, a method of fabricating a LFIA test rapidly and with as little materials as possible is also needed.

SUMMARY

According to a first broad aspect of the present disclosure, a method of fabricating a lateral flow immunoassay (LFIA) using 3D printing comprising: synthesizing and screening at least one peptide antigen; conjugating the peptide antigen with at least one tag; 3D printing a test strip; determining the minimum thickness of a test cassettes; and assembling the LFIA, wherein the peptide antigen binds specifically to at least one analyst, wherein at least one control line and at least one test line are printed on the test line, wherein the material in the test line can bind the complex formed by the analyst and the peptide antigen conjugated with the tag is provided.

According to a second broad aspect of the present disclosure, fusion-peptide for immunoassay comprising at least two epitopes of SARS-CoV-2 is provided, wherein the epitopes are linked by peptide bond.

Other aspects and features of the present disclosure will become apparent to those skilled in the art upon review of the following description of specific embodiments of the invention in conjunction with the accompanying figures.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 1 is a photo showing the CAD of the housing unit design for the first iteration according to an embodiment of the present disclosure.

Figure 16:
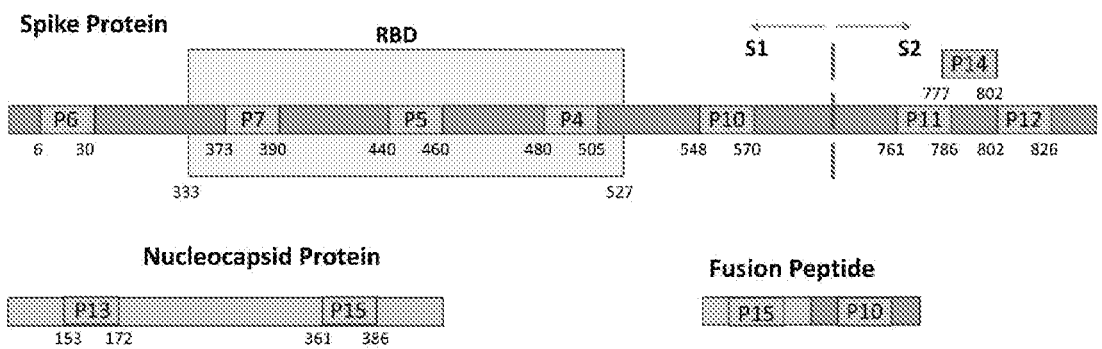

FIG. 16 a graph showing the mapping of the synthesized peptides against the full spike and nucleocapsid protein sequences according to an exemplary embodiment of the present disclosure.

Figure 17:
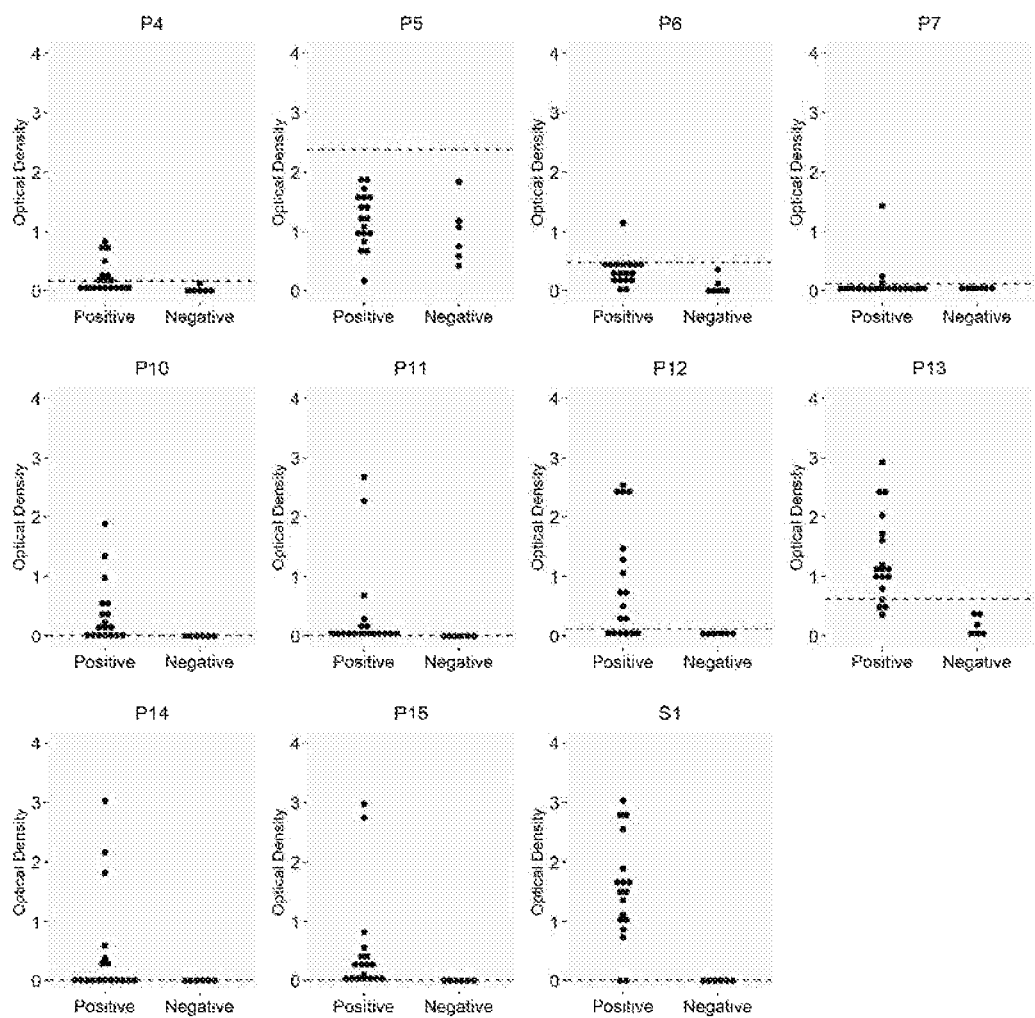

FIG. 17 a graph showing the ELISA experiments screening all 18 IgG positive samples and 6 pre-covid samples with single peptides (P4, P5, P10, P11, P12, P13, P14, and P15) and S1 subunit of the spike protein according to an exemplary embodiment of the present disclosure.

Figure 18:
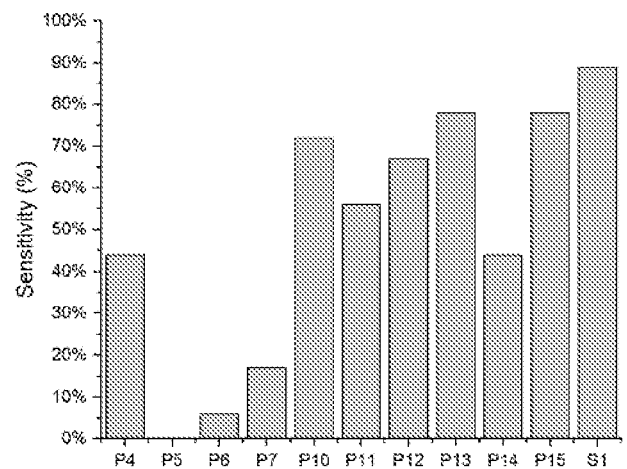

FIG. 18 is a graph showing the sensitivity of the tested peptides in detecting Covid-19 antibodies from positive samples according to an embodiment of the present disclosure.

Figure 19:
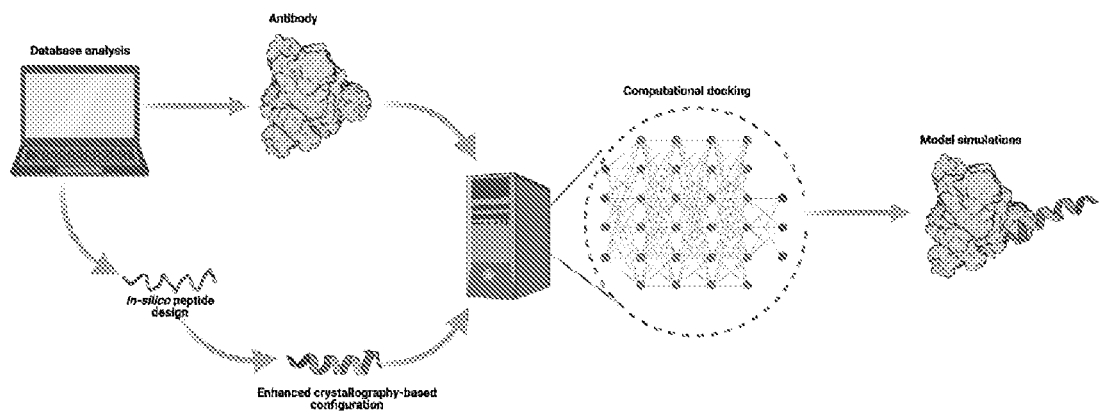

FIG. 19 is a graph showing the graphical flowchart for the docking simulations according to an embodiment of the present disclosure.

Figure 20:
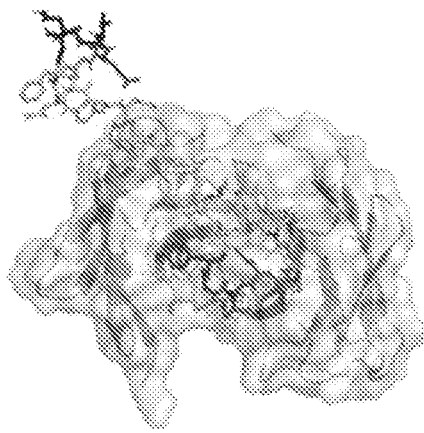

FIG. 20 is a graph showing the docking interaction between P4 peptide and the spike region antibody 7KS9 according to an embodiment of the present disclosure.

Figure 21:
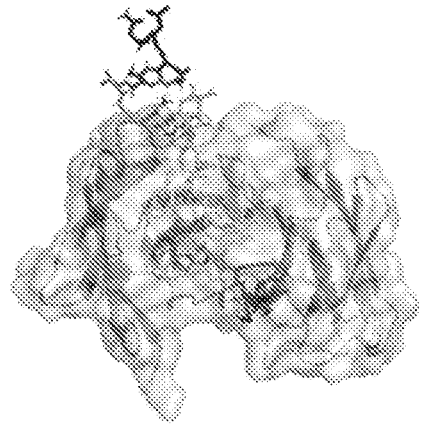

FIG. 21 is a graph showing the docking interaction between P5 peptide and the spike region antibody 7KS9 according to an embodiment of the present disclosure.

Figure 22:
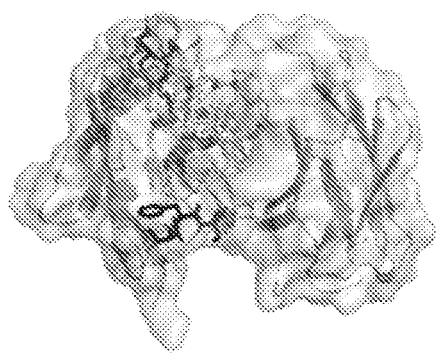

FIG. 22 is a graph showing the docking interaction between P7 peptide and the spike region antibody 7KS9 according to an embodiment of the present disclosure.

Figure 23:
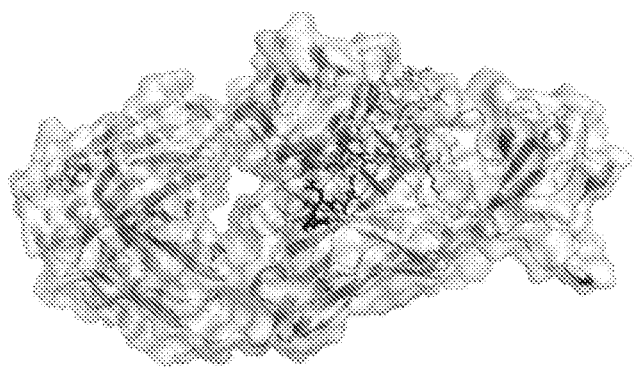

FIG. 23 is a graph showing the docking interaction between P13 peptide and the spike region antibody 7CR5 according to an embodiment of the present disclosure.

FIG. 24 is a graph showing the root mean square deviation of unbound P4 between aligned residues from various protein data banks (PDBs) according to an embodiment of the present disclosure.

FIG. 25 is a graph showing the root mean square deviation of unbound P5 between aligned residues from various protein data banks (PDBs) according to an embodiment of the present disclosure.

FIG. 26 is a graph showing the root mean square deviation of unbound P7 between aligned residues from various protein data banks (PDBs) according to an embodiment of the present disclosure.

FIG. 27 is a graph showing the superimposition model representations of P4, P5, P7 and P13 according to an embodiment of the present disclosure.

Figure 28:
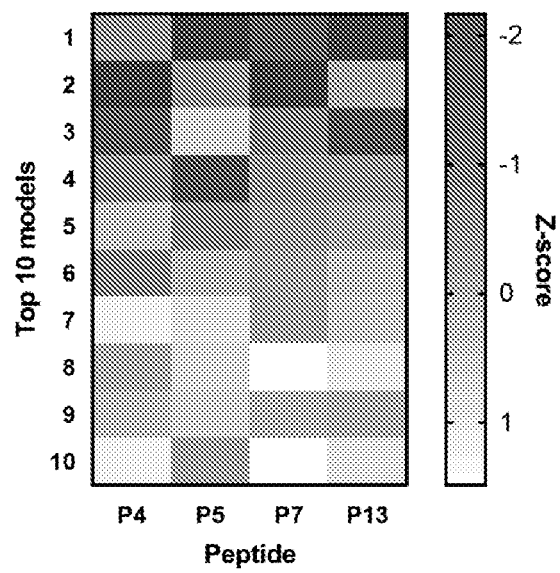

FIG. 28 is a graph showing the top ten generated simulations for the docking between the peptides and antibodies according to an embodiment of the present disclosure.

Figure 29:
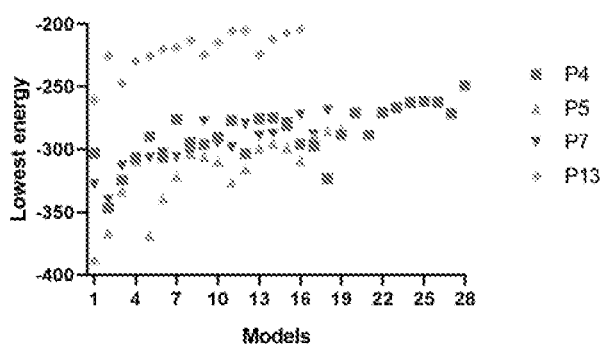

FIG. 29 is a graph showing the maximum number of generated models from each peptide according to an embodiment of the present disclosure.

Figure 30:
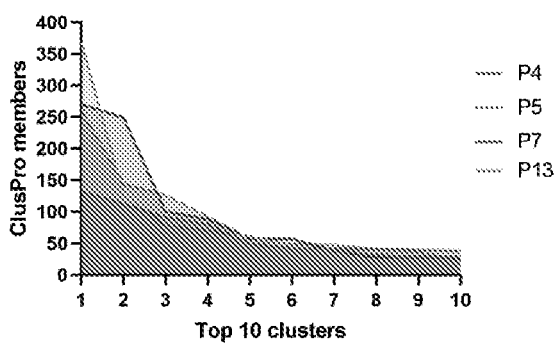

FIG. 30 is a graph showing the amount of information grouped by the ClusPro algorithm and the clusters from models according to an embodiment of the present disclosure.

Figure 31:
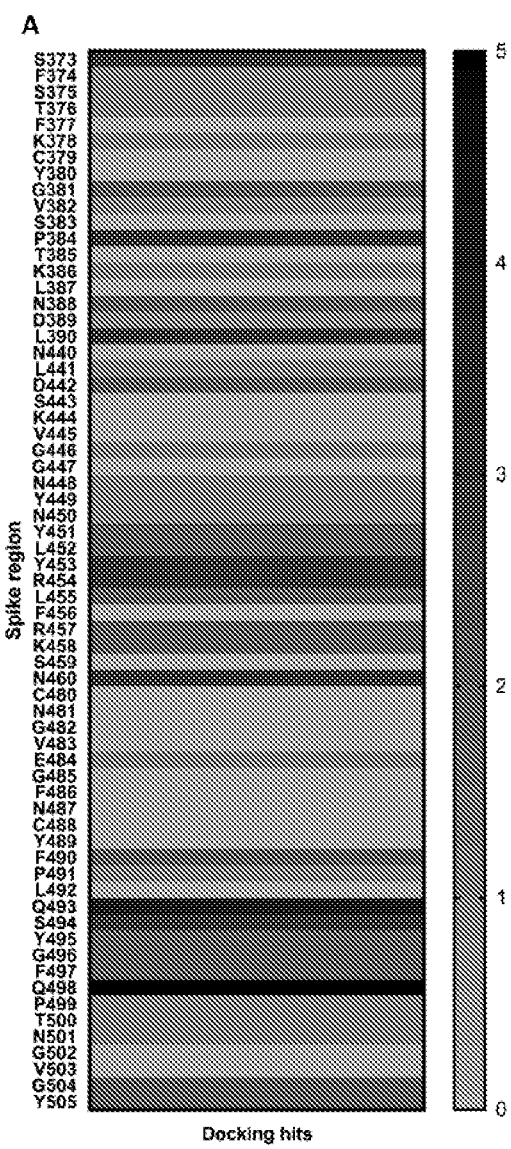

FIG. 31 is a graph showing the docking interactions from the peptides to the spike region according to an embodiment of the present disclosure.

Figure 32:
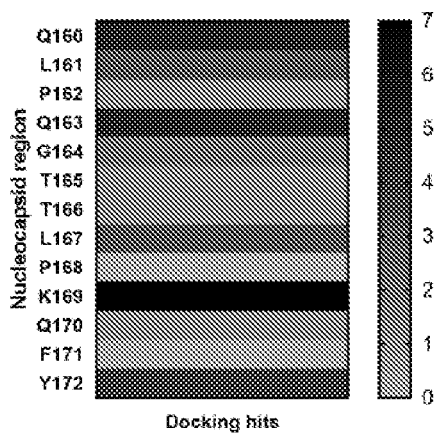

FIG. 32 is a graph showing the docking interactions from the peptides to the nucleocapsid regions according to an embodiment of the present disclosure.

Figure 33:
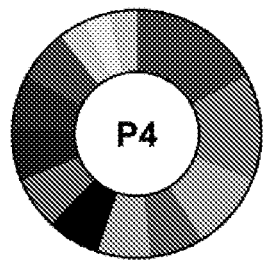

FIG. 33 is a graph showing the interacting amino acids from P4 within the active site of the antibody according to an embodiment of the present disclosure.

Figure 34:
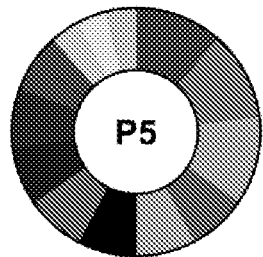

FIG. 34 is a graph showing the interacting amino acids from P5 within the active site of the antibody according to an embodiment of the present disclosure.

Figure 35:
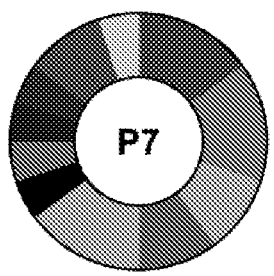

FIG. 35 is a graph showing the interacting amino acids from P7 within the active site of the antibody according to an embodiment of the present disclosure.

Figure 36:
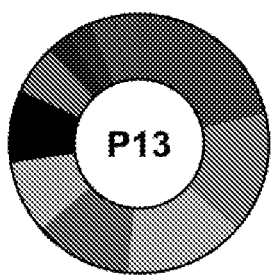

FIG. 36 is a graph showing the interacting amino acids from P13 within the active site of the antibody according to an embodiment of the present disclosure.

Figure 37:
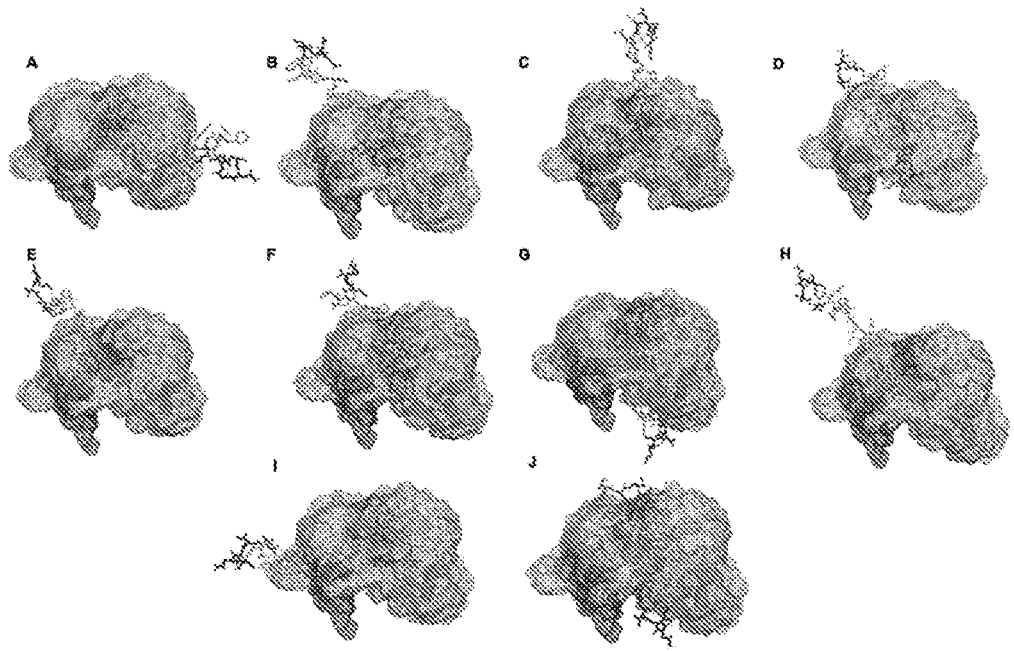

FIG. 37 is a graph showing the top 10 generated simulations for the docking between the P4 and spike region antibody 7KS9 according to an embodiment of the present disclosure.

Figure 38:
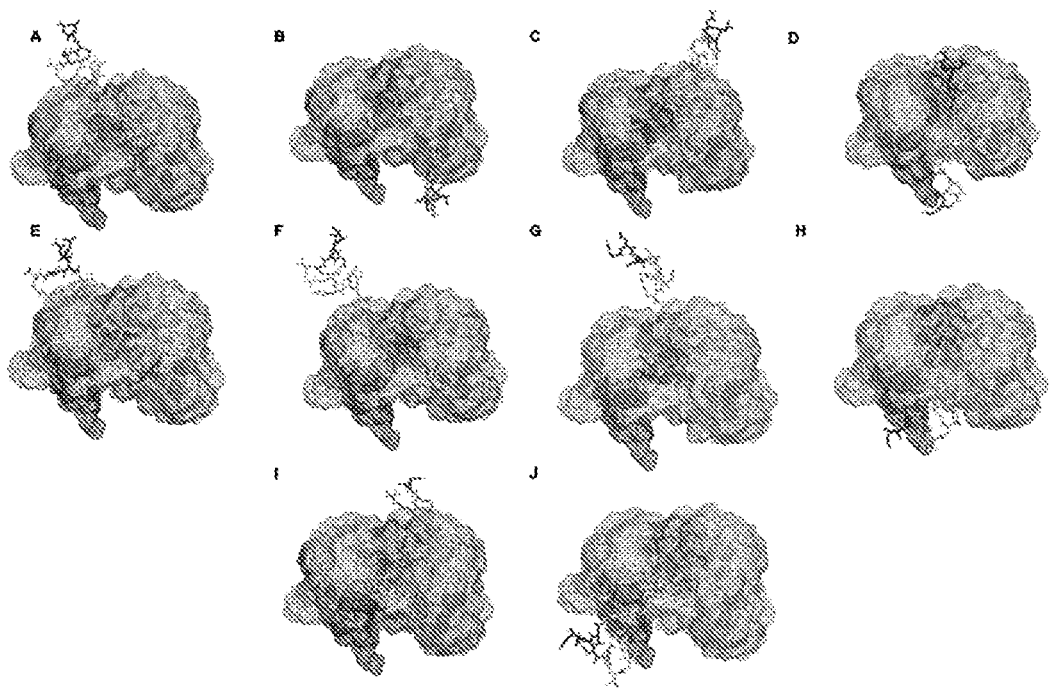

FIG. 38 is a graph showing the top 10 generated simulations for the docking between the P5 and spike region antibody 7KS9 according to an embodiment of the present disclosure.

Figure 39:
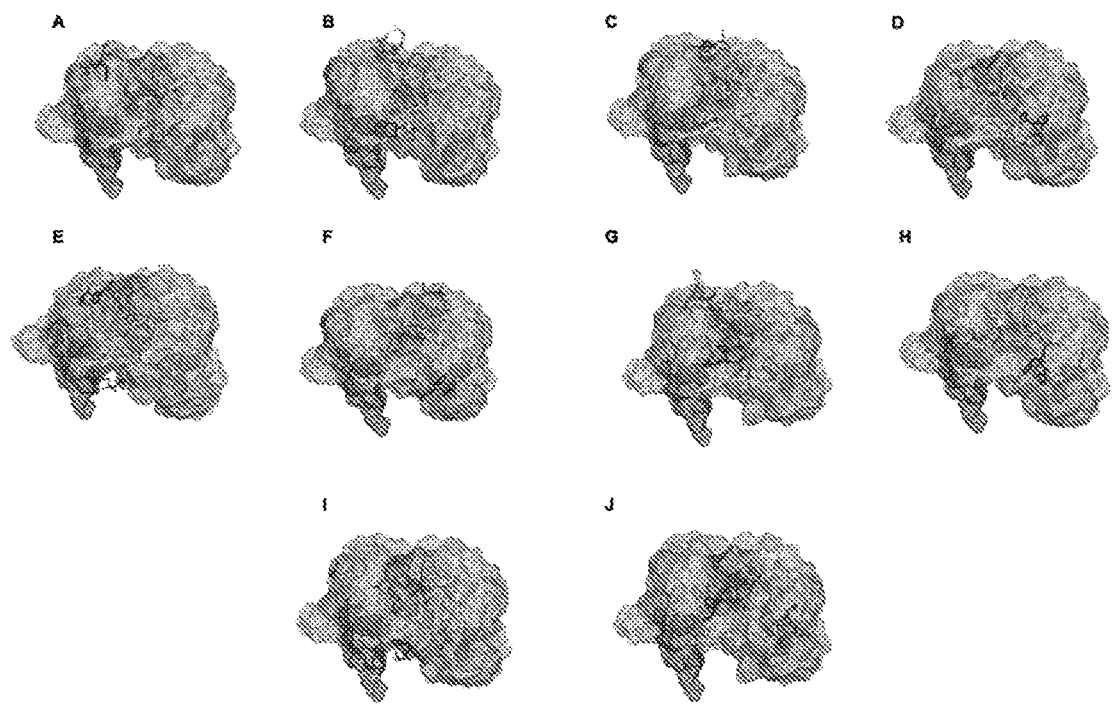

FIG. 39 is a graph showing the top 10 generated simulations for the docking between the P7 and spike region antibody 7KS9 according to an embodiment of the present disclosure.

Figure 40:
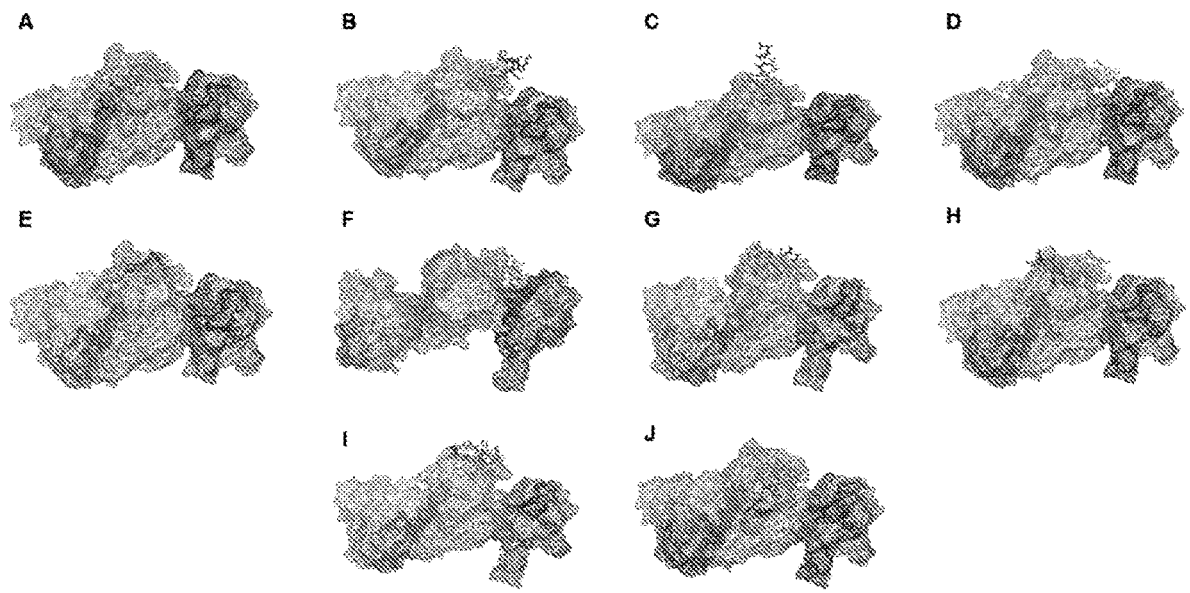

FIG. 40 is a graph showing the top 10 generated simulations for the docking between the P13 and spike region antibody 7CR5 according to an embodiment of the present disclosure.

Figure 41:
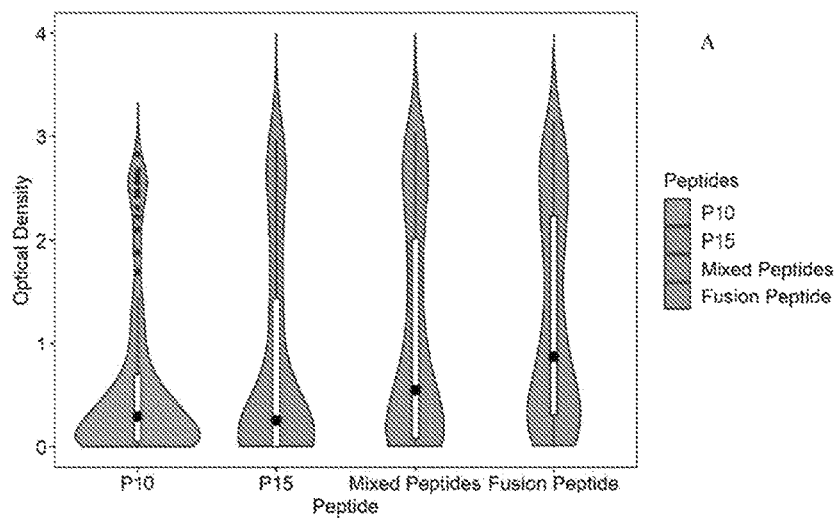

FIG. 41 is a graph showing the Optical Density (OD) results for P10, P15, mixed (P10+P15), and fusion (P10–P15) peptides when tested with 110 IgG positive Covid samples according to an embodiment of the present disclosure.

Figure 42:
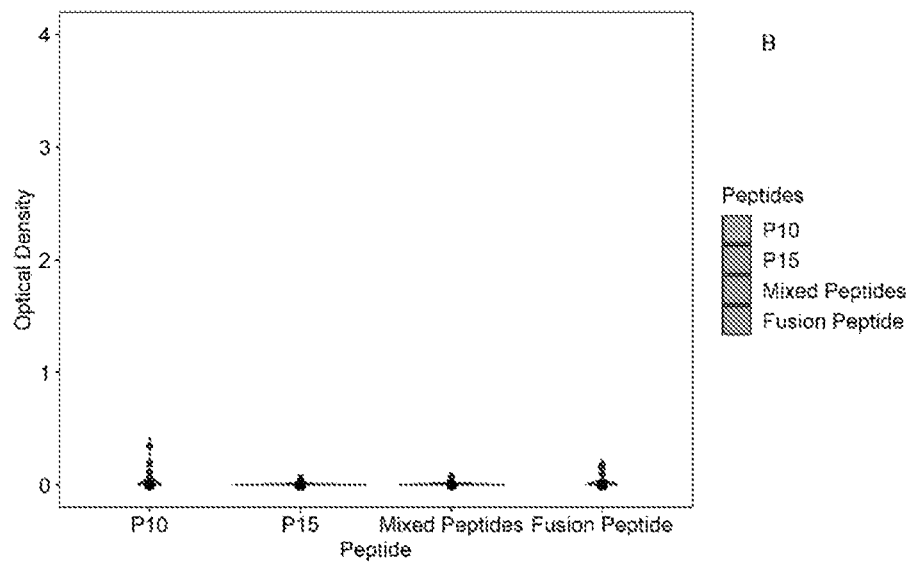

FIG. 42 is a graph showing the Optical Density (OD) results for P10, P15, mixed (P10+P15), and fusion (P10–P15) peptides when tested with 35 negative pre-covid samples according to an embodiment of the present disclosure.

Figure 43:
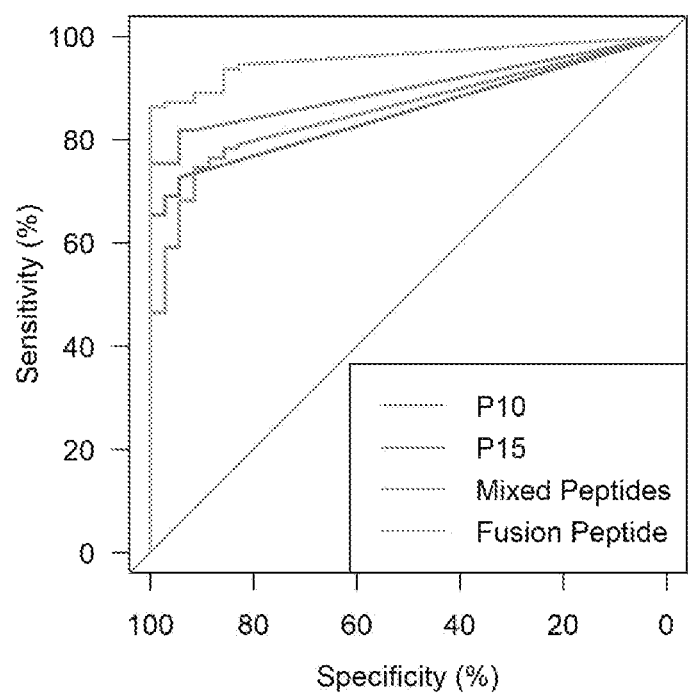

FIG. 43 is a graph showing the ROC curves for P10, P15, mixed (P10+P15), and fusion (P10–P15) peptides according to an embodiment of the present disclosure.

Figure 44:
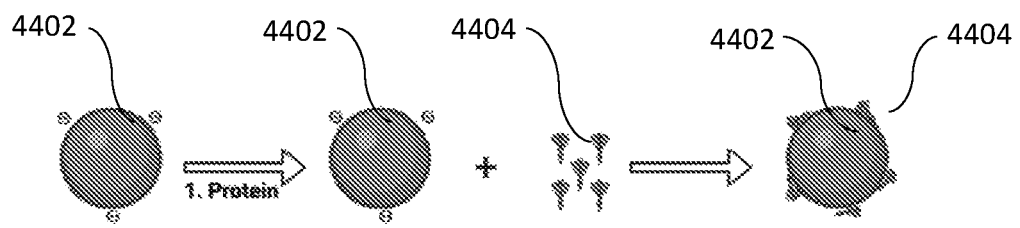

FIG. 44 is a graph showing the schematic representation of the physical conjugation process between the gold nanoparticles and the proteins of interest according to an embodiment of the present disclosure.

Figure 45:
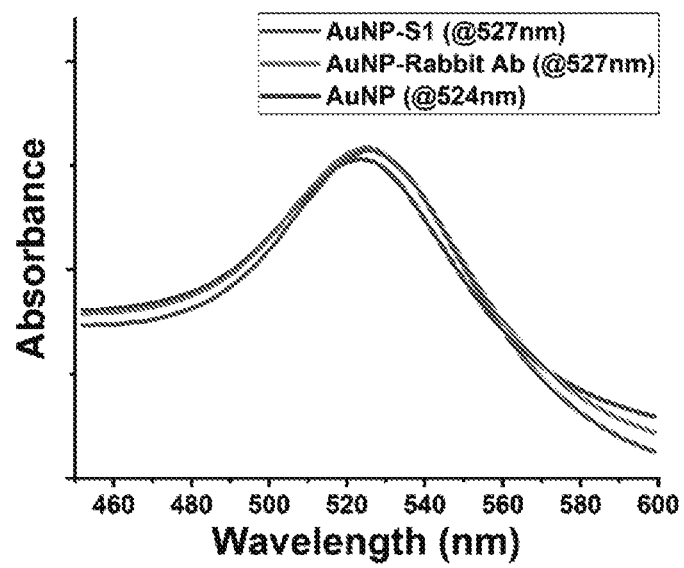

FIG. 45 is a graph showing the detection of conjugated AuNP with antibodies and proteins by UV/VIS spectroscopy according to an embodiment of the present disclosure.

Figure 46:
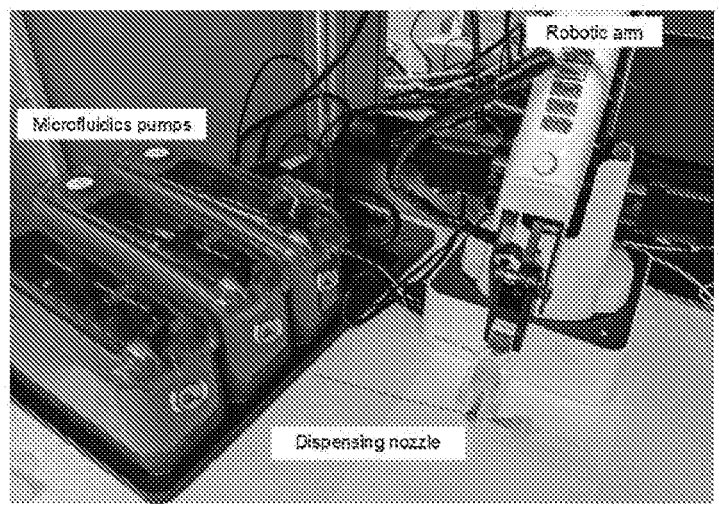

FIG. 46 is a graph showing the printing setup consists of a robotic arm, microfluidics pumps, and dispensing nozzle according to an embodiment of the present disclosure.

Figure 47:
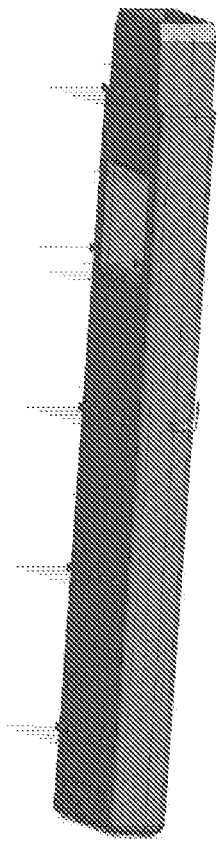

FIG. 47 is a graph showing the force distribution being applied to the cassette during the simulation where one side is fixed according to an embodiment of the present disclosure.

Figure 48:
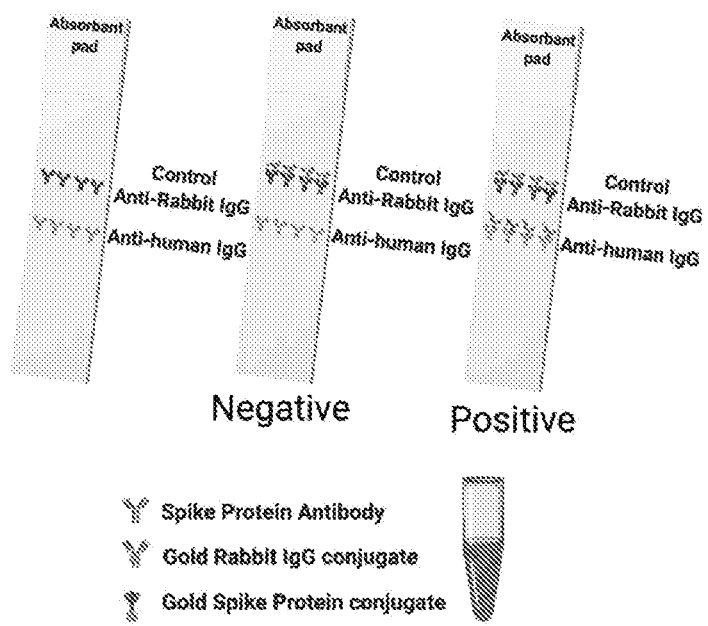

FIG. 48 is an illustration showing an assembled dipstick test using the conjugated gold nanoparticles according to an embodiment of the present disclosure.

Figure 49:
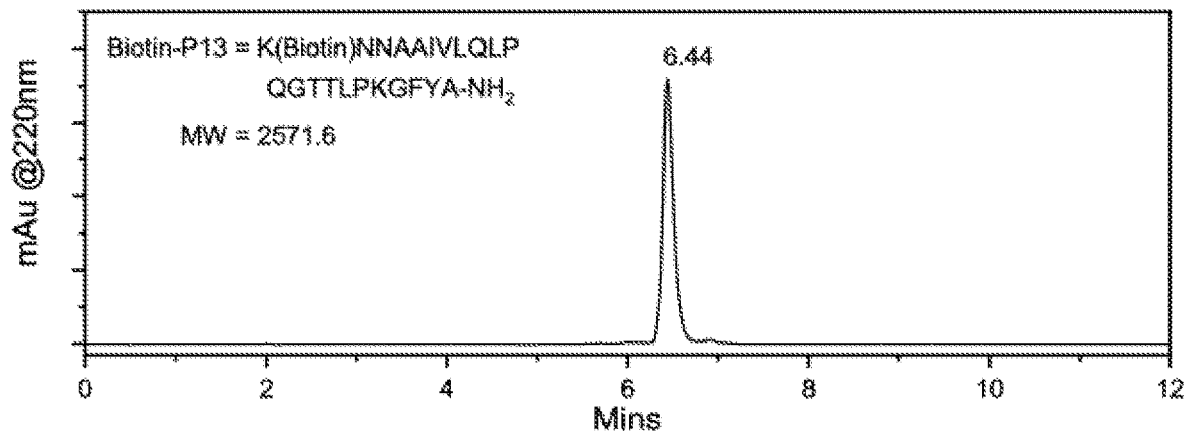

FIG. 49 is a graph showing the liquid chromatogram of biotin-P13 by the absorbance at 220 nm according to an embodiment of the present disclosure.

Figure 50:
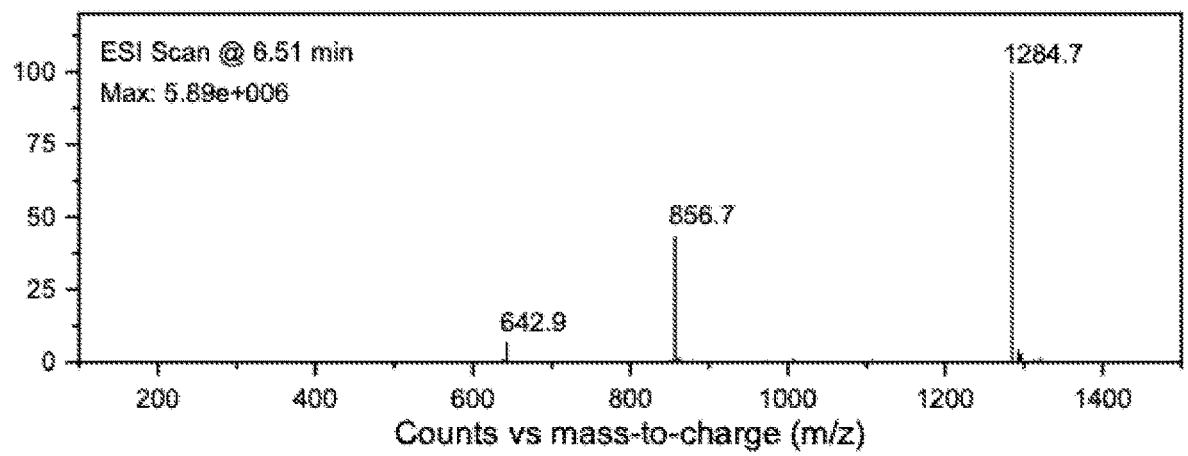

FIG. 50 is a graph showing the mass spectrum of biotin-P13 according to an embodiment of the present disclosure.

DETAILED DESCRIPTION OF THE INVENTION

Definitions

Where the definition of terms departs from the commonly used meaning of the term, applicant intends to utilize the definitions provided below, unless specifically indicated.

Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

For purposes of the present disclosure, the term "comprising", the term "having", the term "including," and variations of these words are intended to be open-ended and mean that there may be additional elements other than the listed elements.

For purposes of the present disclosure, directional terms such as "top," "bottom," "upper," "lower," "above," "below," "left," "right," "horizontal," "vertical," "up," "down," etc., are used merely for convenience in describing the various embodiments of the present disclosure. The embodiments of the present disclosure may be oriented in various ways. For example, the diagrams, apparatuses, etc., shown in the drawing figures may be flipped over, rotated by 90° in any direction, reversed, etc.

For purposes of the present disclosure, a value or property is "based" on a particular value, property, the satisfaction of a condition, or other factor, if that value is derived by performing a mathematical calculation or logical decision using that value, property or other factor.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present disclosure, the term "sensitivity" refers to the probability that a test correctly identifies a true positive sample. Sensitivity can be calculated using formula (1) in Example 17.

For purposes of the present disclosure, the term "specificity" refers to the probability that a test correctly identifies a true negative sample. Specificity can be calculated using formula (2) in Example 17.

For purposes of the present disclosure, the term "accuracy" refers to the probability that a test correctly identifies a true negative sample and true positive samples. Accuracy can be caulculated using formula (3) in Example 17.

For purposes of the present disclosure, the term "epitope" refers to the part of an antigen that is recognized by the immune system.

For purposes of the present disclosure, the term "RBD" refers to receptor-binding domain in SARS-CoV-2 spike protein. The part of the SARS-CoV-2 spike protein corresponding to RBD is illustrated in FIG. 16.

For purposes of the present disclosure, the term "iteration challenge" refers to the size of the first iteration in the absence of the buffer well.

Description

In one embodiment, a successful LFIA test that detects IgG antibodies developed by assembling all the components as detailed below. First, SARS-CoV-2 spike protein was conjugated to gold nanoparticles (AuNP) to capture SARS-CoV-2 antibodies in the sample tube. Then, the testing lines consisting of secondary antibodies were printed on the nitrocellulose membrane to capture primary antibodies, and the strip was placed in a 3D-printed housing cassette after careful design and strain simulation.

In one embodiment, a material extrusion-based 3D bioprinting technique was utilized during the testing strip development where microfluidic pumps and a robotic arm were used to print different antibodies. The microfluidic pump system was used to dispense the capturing material on the nitrocellulose membrane as it offers an easier and efficient way to test multiple proteins. In a preferred embodiment, the capturing material is a secondary antibodies capable of capturing primary antibodies. In a preferred embodiment, the material printed on the nitrocellulose membrane can capture antibodies against SARS-COV-2.

In one embodiment, the robotic arms provide fine control of the nozzle when dispensing the material, while the pumps ensure consistent volume of the material to be dispensed on the nitrocellulose membrane.

In one embodiment, 3D printing was used to fabricate cassettes for rapid in-field assays. 3D printing technology provides the freedom to fabricate and prototype any designs in a standard laboratory setting, and saves the time and effort of many researchers.

In one embodiment, the 3D technologies used to prototype and print the housing unit include material extrusion 3D printing and vat photopolymerization 3D printing. These.

In one embodiment, a LFIA test was developed using multiple technologies to efficiently optimize the testing strips.

In one embodiment, bioprinting and 3D printing techniques were used during the development of a rapid test for the detection of antibodies against various diseases. In a preferred embodiment, the rapid test developed using bioprinting and 3D printing techniques can detect antibodies against COVID-19.

In one embodiment, a material extrusion-based bioprinting setup utilizing a robotic arm was used during the construction of the strips to aid the dispensing of the capturing materials.

In one embodiment, an additive manufacturing technology was used to build a housing unit for the strip in a layer-by-layer manner using photopolymerization technique. The design of the cassette was modified as needed to adapt with the rapid changes in the testing strip during the optimization process.

In one embodiment, the physical strains on the designed cassette was simulated to determine its minimum thickness while ensuring the practicality of use and durability when conducting the test. In a preferred embodiment, the simulation was conducted using finite element analysis (FEA) LFIA Cassette Designs and 3D Printing In one embodiment, the housing unit design went through different iterations for adapting the changes and requirements for the test. In a preferred embodiment, these iterations were designed, fabricated, and assembled in the laboratory using specific requirements.

Figure 1:
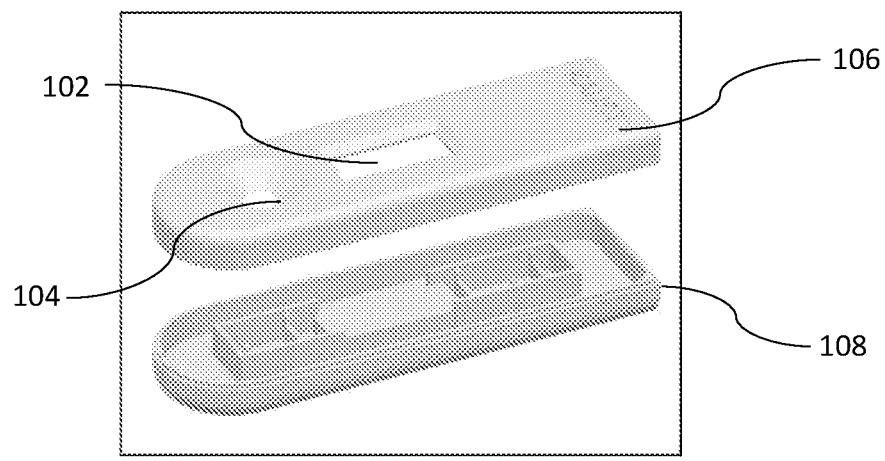
Figure 2:
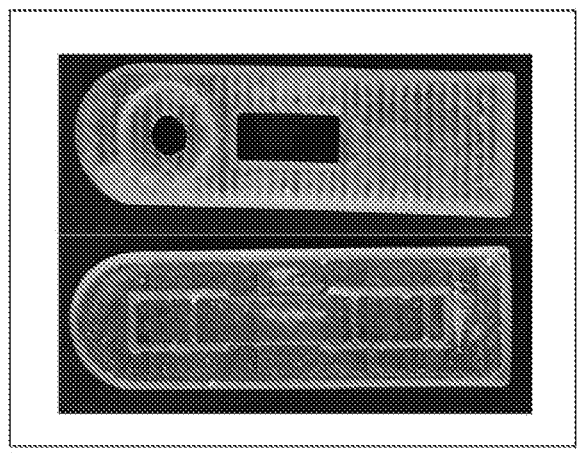
FIG. 2 is a photo showing the 3D printed housing unit for the first iteration according to an embodiment of the present disclosure.

In a preferred embodiment, two iterations are illustrated in FIGS. 1-5. (FIGS. S2 and S3). The iterations shown in FIGS. 1-5 were housing unit for the test designed using NX CAD software. FIG. 1 demonstrates the initial iteration of the CAD design LFIA was designed to suit the geometry and the lateral flow assay requirement. The design shown in FIG. 1 consists of an upper part 106 with only two openings 102 and 104, one for the sample 104 and the other to visualize the tests' results 102 and a lower part 108. Moreover, the lower part 108 was designed to provide support for the strip once added. Furthermore, SLA 3D printing technology was used for prototyping this housing unit, the 3D printed prototype of this design is shown in FIG. 2.

Figure 3:
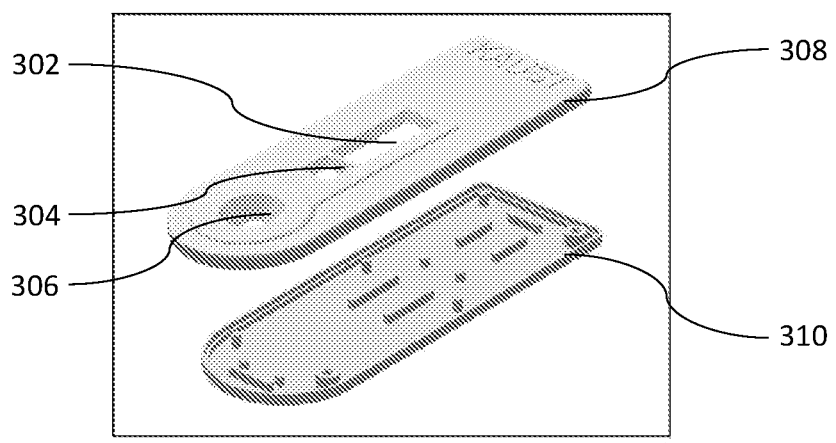
FIG. 3 is a photo showing the CAD of the second iteration design according to an embodiment of the present disclosure.
Figure 4:
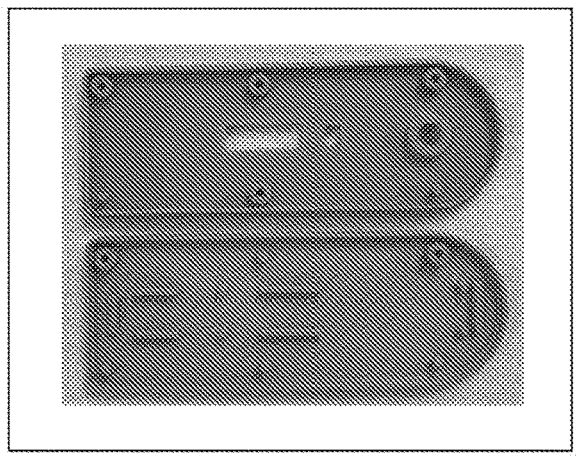
FIG. 4 is a photo showing the 3D printed housing unit of the second iteration using FDM according to an embodiment of the present disclosure.
Figure 5:
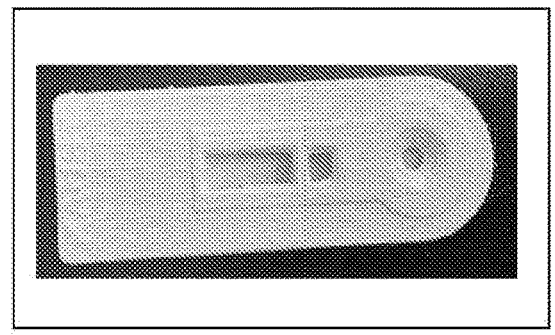
FIG. 5 is a photo showing the 3D printed housing unit of the second iteration using SLA according to an embodiment of the present disclosure.

FIGS. 3-5 demonstrated the second iteration. To further compensate for the first iteration challenges, which is the size of the first iteration and the absence of the buffer well, the housing unit was altered to add a buffer well, as demonstrated in FIG. 3. The reason behind adding a buffer well was to adapt the specific requirement from the lateral flow side. In this embodiment, the buffer well is added into the second iteration, due to the modified sized of the first iteration. The second iteration shown in FIG. 3 has an upper part 308 with three openings 302, 304 and 306, a buffer well 304, a patient sample well 306, and an extended opening for the test's result visualization 302. This iteration was prototyped using two different printing techniques, one using an FDM (Fused deposition modeling) printer as shown in FIG. 4 to take advantage of the printer's heat for a smooth printed surface. SLA (Stereolithography) printer was used as another printing technique to accumulate a higher print quality, as demonstrated in FIG. 5.

In one embodiment, the cassette designs in the above embodiments were made for testing using a full strip setup which includes the conjugate pad.

In another embodiment, the third iteration was a dipstick design which was made to house a strip that does not contain a conjugate pad. This provides a faster way to test the strip by removing an extra step that adds the conjugated AuNP to the conjugate pad.

In one embodiment, two 3D printing technologies were used to print the proposed cassettes. Material extrusion 3D printing technology using thermoplastic filament was developed in the early 1990's.[28] In the material extrusion 3D printing technique, a thermoplastic filament is fused using a mounted motor, which heats and melts the filament to be extruded during the printing process. On the other hand, vat photopolymerization technique uses a liquid photopolymer resin as a printing material, which is subjected to polymerization initiated by a projected laser. This process would selectively solidify the liquid resin against the platform, creating a 3D construct in a layer-by-layer fashion.[29] The advantages of using vat photopolymerization over material extrusion 3D printing are the higher printing resolution and smoother finish surface.[30] Table below provides a summary comparing the two 3D printing technologies, in which PLA refers to Polylactic acid; ABS refers to Acrylonitrile butadiene styrene; ASA refers to Acrylonitrile styrene acrylate; and PETG refers to Polyethylene terephthalate glycol.

| Additive manufacturing technologies | Materials | Speed | Average cost of materials (kg) | Printing resolution | Limitation |
| --- | --- | --- | --- | --- | --- |
| Material extrusion[31, 32] | Plastic filaments (PLA, ABS, ASA, PETG, and nylon) | Fast | Affordable; $40 | Low | Support material |

| Additive manufacturing technologies | Materials | Speed | Average cost of materials (kg) | Printing resolution | Limitation |
|---|---|---|---|---|---|
| Vat photo polymerization[32, 33] | Liquid photopolymers and resins | Slow | Average; $100 | High | Support material and post-curing required |

Figure 6:
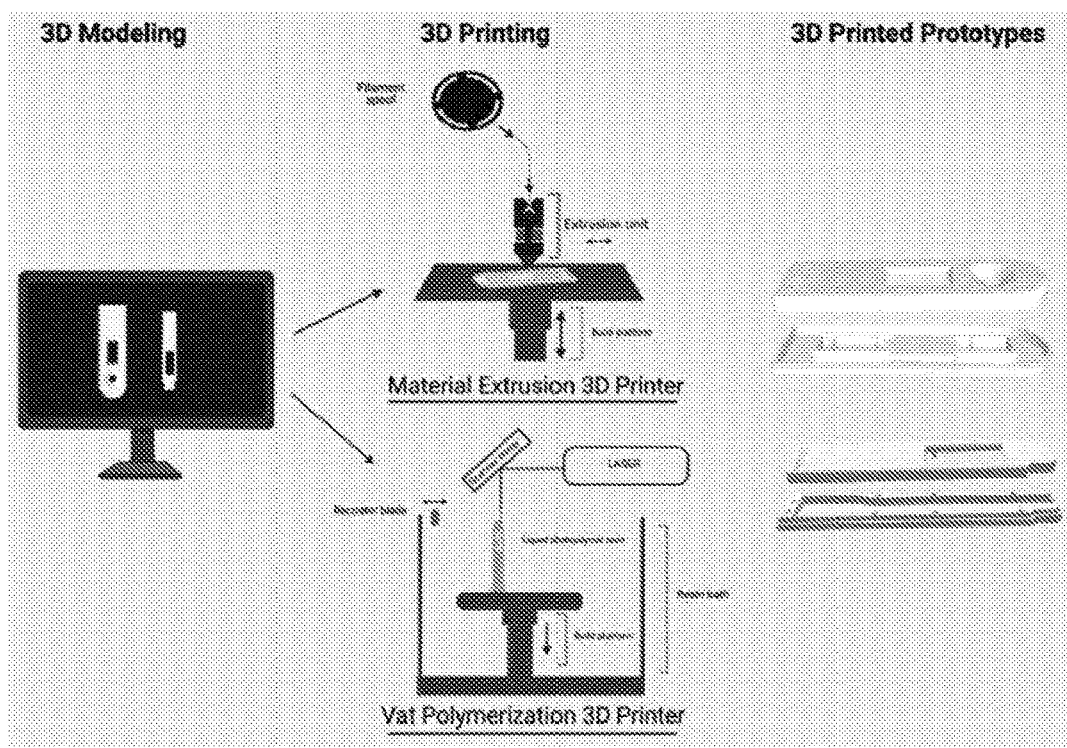
FIG. 6 is a schematic demonstration showing the process used to fabricate the cassettes printed using material extrusion and vat polymerization 3D printing according to an embodiment of the present disclosure.

FIG. 6 demonstrates a schematic of the process used to fabricate the cassettes using the material extrusion and vat polymerization printing methods.

Dipstick Housing Unit

Figure 7:
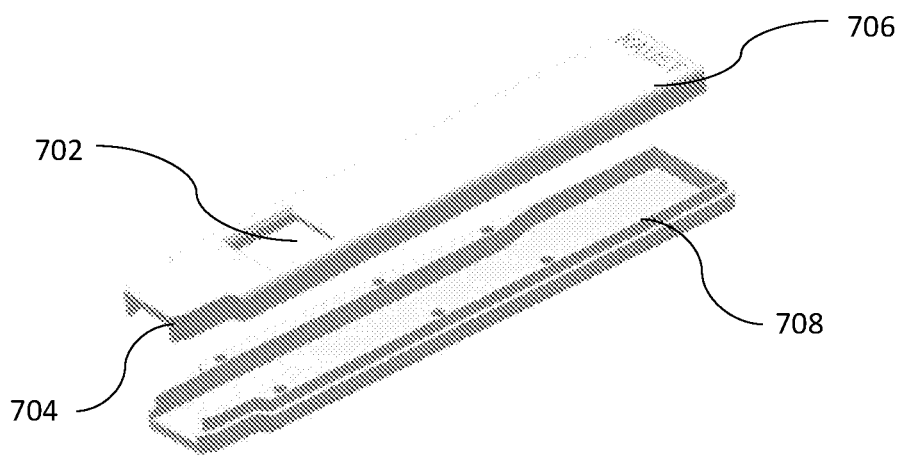
FIG. 7 is a photo showing the CAD of the dipstick housing unit design according to an embodiment of the present disclosure.

In one embodiment, the dipstick housing unit design consists of a smaller unit with an opening 704 from one side to be used for dipping the strip in the test solution as demonstrated in FIG. 7. The design shown in FIG. 7 consists of an upper part 706 with an opening to visualize the tests' results 702 and a lower part 708.

Figure 8:
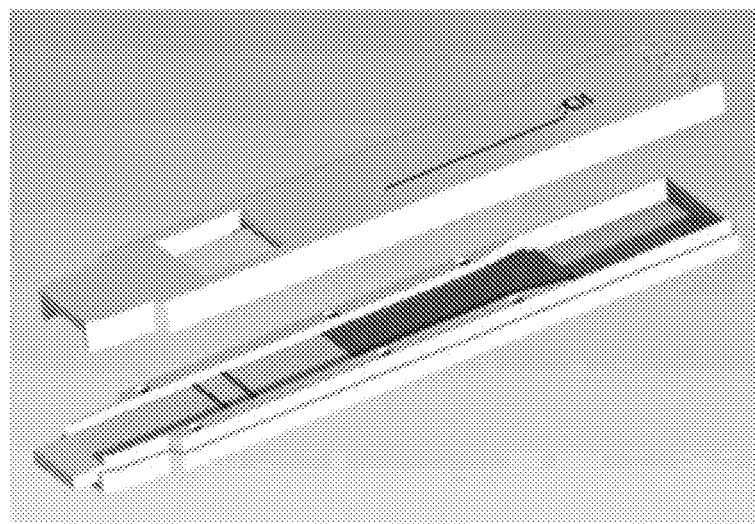
FIG. 8 is a photo showing the CAD of the dipstick housing unit design with testing strip according to an embodiment of the present disclosure.

In one embodiment, this unit was engineered and designed by taking into consideration the security of the testing strip, as shown in FIG. 8.

Figure 9:
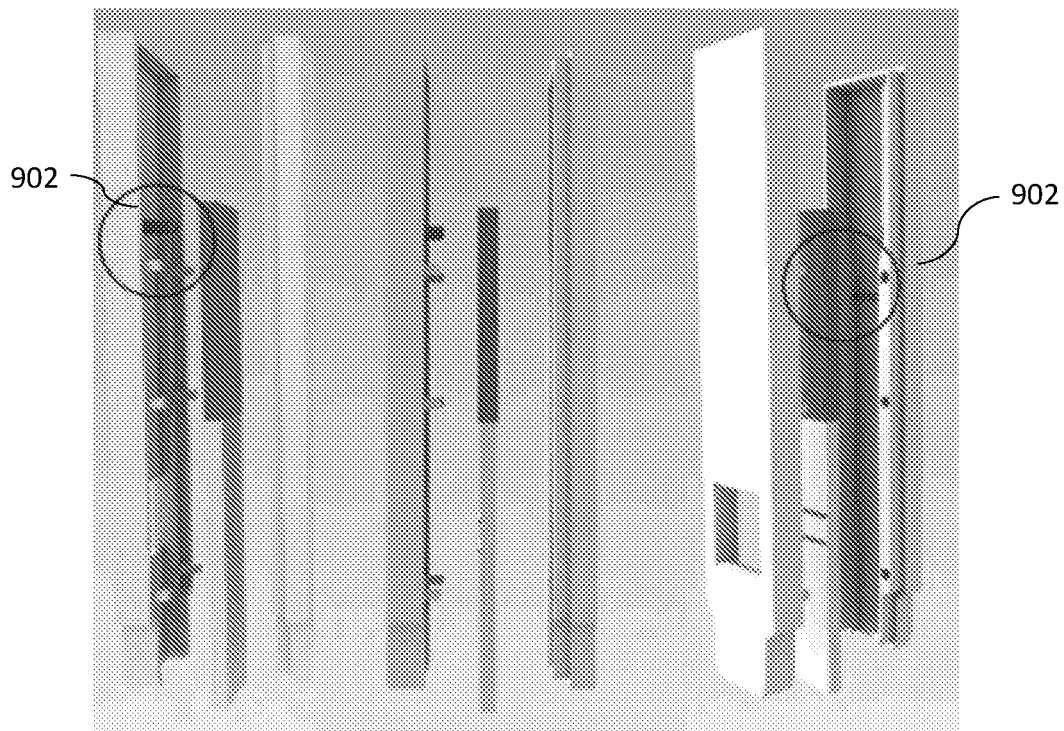
FIG. 9 is a photo showing the CAD of the housing unit design with the bed pressing locking mechanism for securing the bed according to an exemplary embodiment of the present disclosure.

Since this design has a wide opening, it was essential to secure the strip, especially during the testing process. Therefore, in one embodiment, a pressing locking 902 mechanism was designed inside the housing unit, as shown in FIG. 9.

In one embodiment, the dipstick design was 3D printed using Form 3 printer (FormLabs®) while taking into consideration the resolution of the used material.

FEA Simulation for the Final Iteration of the Cassette

In one embodiment, the simulation was conducted on the same software. Therefore, it made the process of changing and modifying the design more straightforward.

In one embodiment, the thickness of the dipstick was changed several times to reduce the use of any unnecessary material in the printing process.

In one embodiment, a cassette with thickness of 0.8 mm was used and printed, and is the minimum thickness needed considering the simulation result.

In one embodiment, the mass applied on the edge of the cassette during the simulation was set to be twice the normal handling force, where the normal handling force was assumed to be 2.5N.

Figure 10:
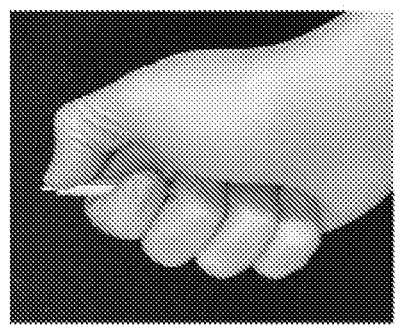
FIG. 10 is a photo showing the assumption and location of the applied force used in the simulation according to an exemplary embodiment of the present disclosure.

In one embodiment, the assumption and location of the applied force were selected based on the actual state of a person applying pressure using one hand, as illustrated in FIG. 10.

Figure 11:
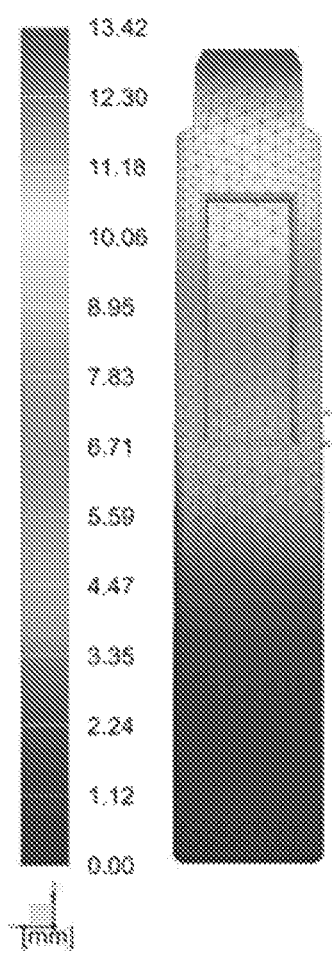
FIG. 11 is a photo showing the simulation of the displacement for the dipstick cassette measured in mm when 5 N force was applied according to an exemplary embodiment of the present disclosure.

In one embodiment, the cassette undergoes deformation with the application of forces. FIG. 11 illustrates the dipstick cassette deformation for the pressing simulation.

In one embodiment, the maximum deformation value was observed to be 13.4 mm. Comparing the deformation result to the dimension of the model, the value range of the deformation is acceptable.

Figure 12:
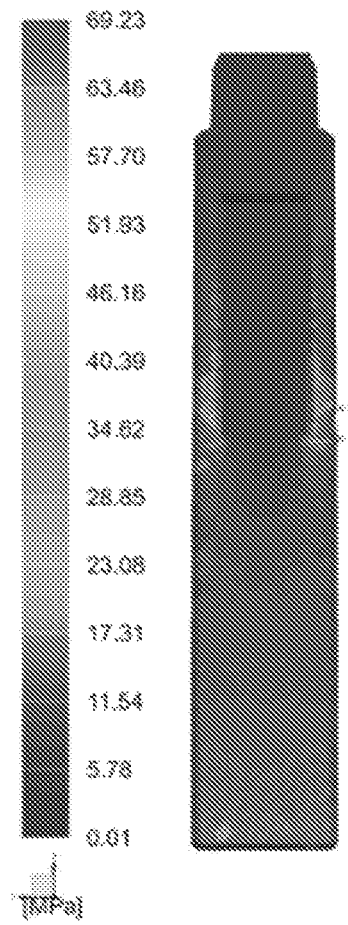
FIG. 12 is a photo showing the simulation of the von Mises stress measured in MPa on the dipstick cassette when 5 N force was applied according to an exemplary embodiment of the present disclosure.

FIG. 12 illustrates the von Mises distribution of stress in the pressing simulation of the dipstick. As shown in FIG. 12, the maximum stress of von Mises was 69.2 MPa. This is slightly lower than the yield strength of the material used in 3D printing which was approximately 70 MPa.

In one embodiment, the dipstick design will tolerate the expected use.

Testing of the Assembled Strip

Figure 13:
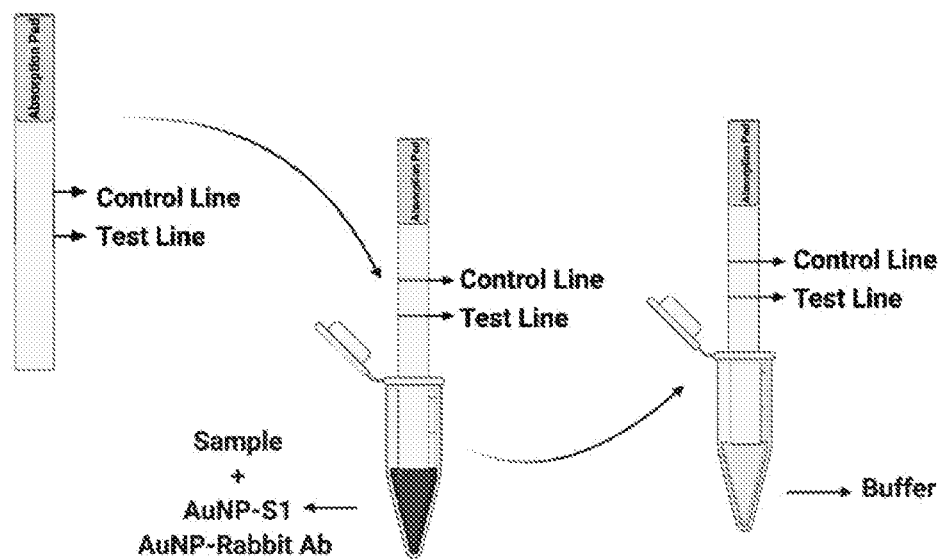
FIG. 13 is a graph illustrating the schematic of the dipping test without the housing cassette according to an exemplary embodiment of the present disclosure.

In one embodiment, LFIA dipstick strips were assembled to be tested with commercial SARS-CoV-2 antibodies to simulate positive or negative tests. The schematic of the test without the housing cassette is illustrated in FIG. 13.

Figure 14:
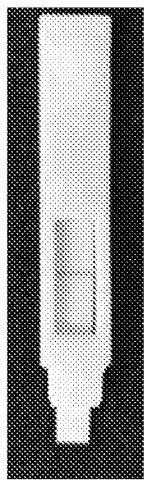
FIG. 14 is a photo demonstrating a LFIA showing a negative signal according to an exemplary embodiment of the present disclosure.

In one embodiment, if only the control line shows a red signal, then the sample is negative, which is shown in FIG. 14.

Figure 15:
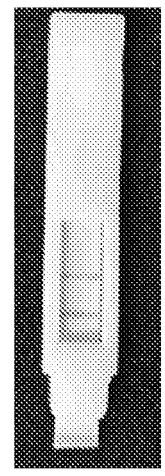
FIG. 15 is a photo demonstrating a LFIA showing a positive signal according to an exemplary embodiment of the present disclosure.

In another embodiment, if both control line and test line show a red signal, then the sample is positive, which is shown in FIG. 15.

In one embodiment, the LFIA provides a faster way to assess the test and ensure that all the test components are working as desired, using a dipstick design in prototyping. When designing a new protein or modifying an existing one to enhance the sensitivity of the test, it is time-efficient to test the conjugated material using a dipstick LFIA before proceeding with further optimization processes to be used as a standard LFIA.

Thus, in one embodiment of the present disclosure, it is demonstrated that the prototyping, printing, and assembly of an LFIA test are feasible using an laboratory developed setup.

In one embodiment, the test cassette could be prototyped to sustain mechanical stress applied to it by hand even if it was designed to be printed with minimum thickness to reduce material.

In one embodiment, bioprinting of the test lines with a robotic arm and microfluidic pump was accurate enough to detect IgG antibodies, when tested with protein-conjugated AuNP and commercially available antibodies.

Additive manufacturing technologies can be a great tool for prototyping and fabricating medical devices and diagnostics tools. These technologies can accelerate the optimization process by quickly adjusting to the designs and then 3D printing the device as needed. During the development phase of a new medical device and diagnostic tools, 3D printing can provide on-demand solutions despite the challenges.

In one embodiment, the peptide epitopes conjugated to AuNP can be used in serological assays to detect SARS-CoV-2 antibodies.

In one embodiment, peptide epitopes from the spike and nucleocapsid proteins with reported immunogenicity[41-43,51, 52] were first synthesized and used to optimize an ELISA test with high sensitivity, specificity, and accuracy. The selected peptides were tested as individuals to determine the sensitivity and specificity for detecting SARS-CoV-2 antibodies.

In one embodiment, a simulation of the docking/binding between the peptide epitopes and the crystal structure of reported SARS-CoV-2 antibodies was performed, which confirmed the interaction between peptide epitope and antibodies and defined the amino acids binding sites.

In one embodiment, the sequences of the peptides were modified to achieve a higher sensitivity level, while not compromising the specificity and accuracy of the peptide-based ELISA and LFIA test.

In one embodiment, sequences from single peptides that showed high sensitivity and specificity were combined and synthesized into one longer peptide, which is a fusion-epitopes peptide. In a preferred embodiment, the single peptides with high sensitivity and specificity were four peptide epitopes that reacted strongly with SARS-CoV-2 antibodies with the highest sensitivity level of 78%.

In one embodiment, tests with the modified peptides improved the sensitivity level of antibodies detection to 88% when fusion-epitopes peptide was used. This data could help in understanding factors that can be utilized to improve the sensitivity, specificity, and accuracy for detecting SARS-CoV-2 antibodies. Furthermore, the result of this study could be used in developing peptide-based serological assays for commercial and clinical use.

Patients' Samples

In one embodiment, a total of 145 patients' serum samples were included in this study consisting of 35 negative pre-covid samples and 110 Covid-19 IgG positive samples. Pre-covid samples were deidentified and archived before November 2019. Regarding the positive samples, 95% were collected between July and September of 2020 and 5% were collected between January and February of 2021. Moreover, females and males represented 55% and 45% of the sample with positive Covid-19 IgG, respectively. The mean age of patients was 40 years (±13.4), and the mean duration between positive PCR test and sample collection was 27.5 days (±13.3).

Screening all Antigens

In one embodiment, 10 peptides listed in the table below were screened with 24 random samples including 18 positive and 6 negative pre-covid samples, to select the peptides with high sensitivity and specificity. The mapping of the synthesized peptides in the table below against the full spike and nucleocapsid protein sequences is shown in FIG. 16.

In one embodiment, the OD values of P5 peptide were high for both positive and negative samples, which resulted in a high threshold value.

In one embodiment, the synthetic peptides show different sensitivity of detecting SARS-CoV-2 antibodies. The sensitivity of the tested peptides in detecting Covid-19 antibodies from positive samples is shown in FIG. 18. As shown in FIG. 18, the highest sensitivity was 78% for nucleocapsid peptides P13 and P15, followed by 72% for P10 and 67% for P12 peptides from the spike protein.

In one embodiment, some patients' samples had higher OD signal with peptides from the nucleocapsid protein while others with the peptides from the spike region.

In one embodiment, all peptides tested and described above had a specificity of 100%. The high specifity for these peptides was a result of the high threshold used to determine positive and negative samples.

In one embodiment, pooling or combining at least two peptides from P4, P10, P11, P12, P13, and P15 could improve the sensitivity for detecting Covid-19 antibodies.

In a preferred embodiment, pooling or combining at least two peptides from P10, P12, P13, and P15 could improve the sensitivity for detecting Covid-19 antibodies.

Docking Simulation

In one embodiment, the peptides interact with antibodies differently. The peptide-antibody interactions were evaluated by an in-silico analysis based on protein docking performed on P4, P5, P7, and P13. The binding and number of interactions between peptides and antibodies are shown in the graphical flowchart illustrated in FIG. 19. Using the

| Peptide | Amino acid sequence | Protein | Amino acid positions |
|---|---|---|---|
| P4 | K(Biotin)CNGVEGFNCYFPLQSYGFQPTNGVGY | S | 480-505 |
| P5 | K(Biotin)NLDSKVGGNYNYLYRLFRKSN | S | 440-460 |
| P6 | K(Biotin) VLLPLVSSQCVNLTTRTQLPPAYTN | S | 6-30 |
| P7 | K(Biotin)SFSTFKCYGVSPTKLNDL | S | 373-390 |
| P10 | K(Biotin)GTGVLTESNKKFLPFQQFGRDIA | S | 548-570 |
| P11 | K(Biotin)TQLNRALTGIAVEQDKNTQEVFAQVK | S | 761-786 |
| P12 | K(Biotin)FSQILPDPSKPSKRSFIEDLLFNKV | S | 802-826 |
| P13 | K(Biotin)NNAAIVLQLPQGTTLPKGFYA | N | 153-172 |
| P14 | K(Biotin)NTQEVFAQVKQIYKTPPIKDFGGFNF | S | 777-802 |
| P15 | K(Biotin)KTFPPTEPKKDKKKKADETQALPQRQ | N | 361-386 |
| P15-P10 | K(Biotin)KTFPPTEPKKDKKKKADETQALPQRQ-SGSGS-GTGVLTESNKKFLPFQQFGRDIA | N-S | 361-386(N)-548-570(S) |

In one embodiment, the interaction between the serum samples and synthetic peptides are tested using ELISA and measured as fluorescent signal intensity (OD signal). The differences in fluorescent signal intensity (OD signal) among the different peptides and S1 subunit of the spike protein are shown in FIG. 17.

In one embodiment, there is a threshold to determine positive and negative OD signals for each peptide. In FIG. 17, the dashed lines represent the threshold for each peptide. As shown in FIG. 17, P4, P10, P12, P13, P15 peptides, and S1 protein had a high number of positive samples above the threshold value.

method illustrated in FIG. 19, the docking interactions between P4, P5 and P7 peptides and the spike region antibody 7KS9 were obtained and shown in FIGS. 20-22, respectively, and docking interaction between P13 peptide and the nucleocapsid antibody 7CR5 is shown in FIG. 23.

In one embodiment, the differences among the initial conformations of P4, P5 and P7 are low, while P13 has a highly variable initial conformation among the proposed initial structures. The initial conformation for the docking was obtained by comparing manually sequence-aligned secondary structures for the same peptide using PyMOL's residue alignment tools. Moreover, root-mean-square deviation was calculated for each conformation, with the results shown in FIGS. 24-26. According to the results shown in FIGS. 24-26, the peptides appear to have a conserved configuration as the average distance between atoms among unbound configurations was 0.6678 Å for p4, 0.6007 Å for p5, and 0.8114 for p7 although the domains of the spike-derived peptides seem to be in their majority random coils.

In one embodiment, the initial conformations have the lowest difference among the complexe 7KS9, as obtained by the root-mean-square deviation. Thus, in a preferred embodiment, the selected configurations were derived from 7KS9 for P4, P5 and P7. The redundancy in this assay had the aim to evaluate if both complexes, although similar in conformation, had different residue interactions with the proposed peptides. The results obtained showed an identical behavior from both antibody complexes, 7KS9, with each peptide of interest. On the other hand, limited data are currently available regarding antibodies complexed to the N-terminal area of the nucleocapsid. Furthermore, representations of the obtained peptides P4 (2702), P5 (2704) and P7 (2706) are shown in FIG. 27.

In one embodiment, the initial conformation of P13 (2708) is also shown in FIG. 27, obtaining from a sequence alignment with the nucleocapsid protein (6M3M).

In one embodiment, all the spike-derived peptides were paired with the antibody 7KS9, after obtaining the initial conformations. In one embodiment, the nucleocapsid derived peptide (P13) was paired with the antibody 7CR5. Using these pairings, the interactions of the spike-derived peptides with 7KS9 and P13 with 7CR5 were further analyzed and shown in FIGS. 28-30.

In one embodiment, the top ten models from each docking simulation, those with the lowest energy according to the Z-Score normalization, were used for further individual analysis. Top ten generated simulations for the docking between the peptides and antibodies is shown in FIG. 28. The maximum number of generated models from each peptide is shown in FIG. 29, while the amount of information grouped by the ClusPro algorithm and the clusters from models is shown in FIG. 30.

In one embodiment, the interactions between the peptide and the active site of the antibody were quantified for both the spike-derived peptides and the nucleocapsid-derived peptide, selected from the top ten clusters. The quantified interactions for the spike-derived peptides is shown in FIG. 31, while the quantified interactions for the nucleocapsid-derived peptide is shown in FIG. 32. The interacting amino acids from each peptide within the active site of the antibody, including 7KS9 for spike and 7CR5 for nucleocapsid are each summarized in FIGS. 33-36.

In one embodiment, P13 and P4 could get the strongest binding, as the top ten clusters presented more interactions (33 and 29, respectively) with 7CR5 and 7KS9 antibodies, respectively, as shown in FIGS. 36 and 33.

In one embodiment, as shown in the heat map in FIG. 31, the zone with the highest interactions from the original spike protein prevails in the C-terminus section of the RBD, specifically in the amino acids Q493 and Q498, which corresponds to the location of P4. In another embodiment, this interaction analysis is inconclusive since P13 is the only nucleocapsid-derived peptide, leaving no space for comparisons with other nucleocapsid peptides, as shown in FIG. 32.

In one embodiment, P13 should be the peptide with the strongest binding from all of them, followed by P4s, P5s, and P7s, from the above analysis.

In one embodiment, all RBD-derived peptides are less reactive, compared to the peptide from the nucleocapsid, which is confirmed in silico.

In one embodiment, the docking representation of each of the top ten simulations between each peptide and the antibodies including 7KS9 and 7CR5 were generated and demonstrated in FIGS. 37-40.

In one embodiment, the simulation was used as a complementary tool to confirm the binding between the peptide epitopes and anti-RBD and anti-nucleocapsid antibodies.

In one embodiment, the peptide epitopes are selective for SARS-CoV-2 antibodies but do not interact with control antibodies, according to the results of the simulation.

In one embodiment, the results obtained from screening all the peptides correlated well with the docking simulation data.

In one embodiment, the Nucleocapsid peptide P13 had the highest sensitivity and the highest number of interactions among the tested peptides in the docking simulation.

In another embodiment, peptides from the RBD region and P6 peptide, which is derived from spike N-terminal domain, had a lower sensitivity compared to other peptides when tested with ELISA.

In one embodiment, among RBD peptides including P4, P5, and P7, P4 was found to have the highest number of interactions with the antibodies and the highest sensitivity in ELISA.

The above description is consistent with the other published studies in which most of the peptides that were found to detect SARS-CoV-2 antibodies with high sensitivity were from outside the RBD region.[41, 41, 53] Additionally, peptide epitopes that elicit antibodies response and can be used as a potential target for vaccine development were also from outside the RBD region.[54] Li et al. suggest that the confirmation of the RBD protein could be the reason these epitopes are less reactive to serum antibodies.[48]

Screening all Samples

In one embodiment, peptides with the highest sensitivity and specificity are P10 and P15 peptides.

In one embodiment, P10 and P15 peptides were selected from the peptide screening and tested with all 110 positive Covid-19 and 35 negative pre-covid samples.

In another embodiment, a fusion-epitopes peptide combining the sequences of P10 and P15 peptides was synthesized as one long peptide.

In one embodiment, were tested with single (P10, P15), mixed (P10+P15), and fusion (P15-P10) peptides had a statistically significant difference in fluorescence signal intensity between positive and negative pre-covid samples (p-value <0.0001), when tested with all patients' serum samples. The optical density results of single, mixed and fusion peptides with positive samples are shown in FIG. 41, while the optical density results of single, mixed and fusion peptides with negative samples are shown in FIG. 42. Black dot in the middle of the box plot in FIGS. 41 and 42 represents the median and violin plot were drawn with kernel density estimate.

In one embodiment, the fusion-epitopes peptide is a better antigen for the detection of antibody compared to non-fused peptides, since the fusion-epitopes peptide had a higher OD signal when compared to all other peptides. Statistical comparison showed significantly higher OD for the fusion-epitopes peptide when compared with P10 (p-value <0.0001), P15 (p-value <0.0001), and mixed P10+P15 (p-value <0.05), as shown in FIGS. 41 and 42.

In one embodiment, the fusion-epitopes peptide had the highest Area Under the Curve (AUC) compared to all other peptides, as shown in the receiver operating characteristics (ROC) curve in FIG. 43. An ROC curve, is a graphical plot that illustrates the diagnostic ability of a binary classifier system as its discrimination threshold is varied. ROC curves were generated for all peptides, and AUC was calculated for each curve. According to FIG. 43, AUC for P10 was 0.857 (95% confidence interval: 0.801-0.907), P15 was 0.852 (95% confidence interval: 0.807-0.896), mixed peptide was 0.898 (95% confidence interval: 0.866-0.936), and fusion-epitopes peptide was 0.958 (95% confidence interval: 0.929-0.984). Each peptide's sensitivity, specificity, and accuracy were determined using the optimal Youden's index from ROC curves. Consistent with the AUC findings, the fusion-epitopes peptide had the highest sensitivity (88.2%), specificity (100%), and accuracy (91.0%) in comparison to P10, P15, and mixture (P10+P15) peptides, which are summarized in the table below.

|  | P10 | P15 | Mixed peptide P10 + P15 | Fusion-epitopes peptide P10 − P15 |
|---|---|---|---|---|
| Sensitivity | 76.3% | 70.9% | 80% | 88.2% |
| (95% CI) | (64.5-84.5%) | (60-80%) | (70-88.1%) | (80.9-96.3%) |
| Specificity | 91.4% | 100% | 100% | 100% |
| (95% CI) | (82.9-100%) | (91.4-100%) | (91.4-100%) | (91.4-100%) |
| Accuracy | 79.3% | 77.2% | 84.1% | 90.3% |
| (95% CI) | (71.7-86.2%) | (69.7-84.1) | (77.2-90.3%) | (85.5-95.9%) |

A mixture of peptides can potentially improve the sensitivity and specificity for detecting Covid-19 antibodies based on information obtained using bioinformatics tools.[43] The sensitivity could reach 100% when using a mixture of 4 peptides.[43] This enhancement in sensitivity and specificity can also be achieved for a chemiluminescent immunoassay that uses multiple antigens for detecting Covid-19 antibodies.[55] This is consistent with the findings in the present disclosure, in which we experimentally demonstrated that the sensitivity and specificity increase when using a mixture of multiple peptides.

In one embodiment, a fusion-epitopes peptide combining sequences from different viral protein regions would further improve the sensitivity and specificity. Combining different sequences has been demonstrated, in which cell-penetrating peptides were combined with peptides that have DNA binding activities in order to design multifunctional peptides.[56]

SARS-CoV-2 is an RNA virus that is susceptible to mutations. Since the beginning of the pandemic, several mutations have been identified; four have been identified as variants of concern by the WHO, which are Alpha, Beta, Gama, and Delta, which are summarized in the table below.[24]

| Variant | Peptide | Mutation | Protein |
|---|---|---|---|
| Alpha | P4 | N501Y | Spike |
|  | P10 | A570D | Spike |
| Beta | P4 | E484K | Spike |
|  | P4 | N501Y | Spike |
| Gamma | P6 | L18F | Spike |
|  | P6 | T20N | Spike |
|  | P6 | P26S | Spike |
|  | P4 | E484K | Spike |
|  | P4 | N501Y | Spike |
| Delta | P5 | L452R | Spike |
|  | P15 | D377Y | Nucleocapsid |

In one embodiment, the amino acids sequences used in the immunoassays in the present disclosure are changed as a result of some of the mutations in these variants.

In a preferred embodiment, the Alpha variant has resulted in a change to the spike protein that affected the P10 peptide (A570D), and the Delta variant has resulted in a change to the nucleocapsid protein that affected the P15 peptide (D377Y).[57]

In one embodiment, using a fusion-epitopes peptide containing multiple sequences from different variants minimize the impact of mutations in amino acid sequences and detect antibodies against any variant.

In one embodiment, antigens in the present disclosure either as individual or fusion-epitopes peptides could be used to develop serological tests for commercial applications.

In one embodiment, the serological test is an ELISA test similar to examples in the present disclosure. In a preferred embodiment, the ELISA test is developed as an already coated plate to detect serum antibodies in all clinical laboratories.

In another embodiment, magnetic beads is conjugated with the above described peptide epitopes to detect serum antibodies using a magnetic chemiluminescence immunoassay which is used in more advanced clinical laboratories.[58]

In another embodiment, the above described peptide epitopes could be used to develop rapid serological tests to detect SARS-CoV-2 antibodies. In a preferred embodiment, a Lateral Flow Immunoassay (LFIA) can be developed for the rapid detection of SARS-CoV-2 antibodies.[59] In another embodiment, conjugating peptide epitopes to gold nanoparticles could be used as a nanosensor for rapid detection of antibodies by a colorimetric assay.[60]

In one embodiment, these rapid tests can be used as point-of-care tests where access to a clinical laboratory is limited.

In one embodiment, several peptide epitopes from the SARS-CoV-2 spike and nucleocapsid proteins and identified several peptide epitopes were tested and can be used to detect serum antibodies with high sensitivity and specificity. The experimental results were consistent with docking simulations in which a higher number of interactions between the antibodies and peptides corresponded to higher detection sensitivity using ELISA.

In another embodiment, combining amino acid sequences from different epitopes into one peptide enhanced the sensitivity and specificity of the test compared to a single or mixture of peptides.

In a preferred embodiment, peptide epitopes are used to design immunoassays to detect Covid-19 antibodies either as a point of care or laboratory-based tests.

In one embodiment, due to the flexibility of peptide synthesis, peptide epitopes could be modified to reflect changes in the SARS-CoV-2 sequence due to mutations. In a preferred embodiment, fusion-epitopes peptides could also be designed to detect antibodies from different variants of SARS-CoV-2.

Having described the many embodiments of the present disclosure in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Example 1

Materials

Forty nanometers Gold NanoSpheres 2 mM citrate (OD=1) was purchased from Nanohybrids®. SARS-CoV-2 (2019-nCoV) Spike S1-His Recombinant Protein (HPLC-verified) (Cat. No.: 40591-V08H) and Normal Rabbit Control IgG (Cat. No.: CR1) were purchased from Sino Biological®. SARS-CoV-2 Spike Protein (S-ECD/RBD) Monoclonal Antibody (bcb03) (Cat. No.: MA5-35950) and Goat Anti-Rabbit IgG (H+L) Superclonal Secondary Antibody (Cat. No.: A27033) were purchased from Fisher Scientific®. Mouse monoclonal (JDC-10) Anti-Human IgG Fc (HRP) (Ab99759) was purchased from Abcam®. 1×Phosphate-buffered saline (PBS), sucrose, TWEEN 20, and bovine serum albumin (BSA), potassium carbonate, and Tris buffer were purchased from Sigma-Aldrich®. All chemicals were used as received, without purification or modification. Cellulose fiber sample pads, glass fiber conjugate pads, and high-flow nitrocellulose membrane were purchased from EMD Millipore® Corporation. Sample pads, conjugate pads, and absorbent pads of different sizes were purchased from Ahlstrom-Munksjo. Backing cards KN-2211® were purchased from Kenosha. FormLabs® Photopolymer Resin White (FLGPWH04) was purchased from FormLabs®.

Example 2

Conjugation of the Gold Nanoparticles

To conjugate the gold nanoparticles (AuNP) (4402) with S1 spike protein (4404) (40591-V08H, Sino Biological®) and Rabbit antibody, as shown in FIG. 44, 1 ml of 1 OD AuNP solution was used and the pH was adjusted to 8.5-9 using potassium carbonate ($K_2CO_3$). The protein was added to the AuNP suspension at a ratio of protein solution:AuNP solution of 1:100 (v:v) with a final protein concentration of 10 μg/ml, and the suspension was incubated for 2 h while mixing. Then, 250 μl of 5% BSA in TRIS buffer was added and mixed for an additional 15 min. Afterward, 100 μl of 1% TWEEN 20 in TRIS buffer was added to the suspension and centrifuged for 10 min at 8000×g and 4° C. The supernatant was removed, and the precipitate was resuspended in 1 ml of Tris buffer (pH 8.5)+1% BSA+1% TWEEN 20 and centrifuged as before. Finally, the precipitate was resuspended in 100 μl of Tris buffer (pH 8.5)+1% BSA+1% TWEEN 20+20% sucrose to achieve a conjugated AuNP concentration of 10 OD. The same process was used when conjugating the S1 spike protein and rabbit antibodies to the AuNP.

To confirm the conjugation of the protein to the gold nanoparticles, UV-Vis Spectrometer (PerkinElmer® Lambda 1050) was used to compare the UV-Vis spectra of the conjugated AuNP with ligand-free AuNP. The red shift in peak absorbance between the conjugated AuNP and ligand-free AuNP was assessed, which can be used to confirm the conjugation. The sample was scanned from 800 nm to 250 nm with a data interval of 1 nm and a scanning speed of 266.75 nm/min. To assess the attachment of the proteins to the gold nanoparticles, UV-VIS absorption scan was performed, in which AuNP-S1, AuNP-rabbit antibody conjugates to ligand-free AuNP were compared. The conjugated nanoparticles showed a 3 nm shift compared to the ligand-free nanoparticles, as shown in FIG. 45, indicating the success of the functionalization of the 1 mL gold nanoparticles to the 10 μg of the S1 protein, and rabbit antibody[25]. The red shift in peak absorbance is an indication of the enlargement of the gold nanoparticle size from the attachment of the proteins to the nanoparticle[26].

Example 3

Assembly of the Strip

To assemble the strip, first, the high-flow nitrocellulose membrane was mounted on the backing cards. Dispensing of the antibodies to the nitrocellulose membrane was done using a setup consisting of a robotic arm (Dobot® Magician, Dobot®, China) and a microfluidic pump (ExiGo®, Cellix, Ireland), as depicted in FIG. 46. this setup could be considered as material extrusion-based bioprinting. Dispensing of the antibodies onto the nitrocellulose membrane was done using a 21 G needle attached to the robotic arm. The antibodies were dispensed at a rate of 200 μl/min and the robotic arm was programmed to move at a speed of 17 mm/s; antibodies were diluted in 1×PBS to be dispensed at a concentration of 200 μg/ml. These parameters ensured that antibodies were dispensed in a thick and continuous line. In particular, two antibody lines were printed on the nitrocellulose membrane. A test line was printed with anti-human antibodies (Abcam®, Ab99759) and a control line was printed with anti-rabbit antibodies (Fisher Scientific®, A27033). The strip was then dried at room temperature for 1 h. Then, the absorption pad was added to the backing card with a 2-3 mm overlap with the nitrocellulose membrane. Finally, the assembled backing card, nitrocellulose membrane, and absorbent pad were cut into 5 mm wide strips.

Example 4

Designing and 3D Printing of the LFIA Strip Cassettes

NX computer-aided design (CAD) software was used in designing the housing units, along with SolidWorks® as a supporting program. NX CAD was mainly used to design several iterations due to its capability in designing small features. NX CAD provided the simulation tools needed to test the assembly of the design before printing; the simulation of the designed structure was needed to design the locking mechanism as it requires a precise sizing to ensure proper locking after printing.

Multiple 3D printing technologies were used to ensure the design's maximum potential in prototyping these small housing units. Material extrusion 3D printing is the traditional 3D printing method, and vat photopolymerization 3D printing was used in prototyping the cassette designs. Using vat photopolymerization, 3D printing was about its ability to print a small housing unit with fine features in a short period of time. Furthermore, cassettes were printed with FormLabs® white liquid resin and commercially available thermoplastic filament to keep the housing unit price reasonable. The vat photopolymerization 3D printer, FormLabs® (Form 3), which was used in printing the housing unit, is capable of printing a hundred units a day.

Several design iterations were devolved to complement the rapid changes during the test development. The first iteration of the designs started with mimicking the commercially available rapid tests[27]. While modifying the test, the cassette design was modified as well leading to the final iteration design. Using different 3D printing technologies allowed the testing and changing of different features while developing the test.

Example 5

FEA Simulation for the Final Iteration of the Cassette

LFIA test strips are usually single-use tests, and the housing units are there to protect the strip. The designing process in the present disclosure was to reduce the amount of material needed to build the cassette, thus reducing wasted and discarded material from each cassette used. FEA simulation was used to study the proposed design before printing to ensure that the design can sustain handling forces without breaking. The durability of the cassette is not essential in single-use devices. However, a minimum thickness for the proposed cassette is required to prevent it from breaking during the test and handling when polyethylene is used as a material for the designed cassette.

The FEA simulation was conducted using NX software. As NX was the CAD software used to design the cassette, it was also used to perform the FEA simulation to ensure accurate simulations results for the proposed design. Furthermore, before FEA simulation, the two sides of the cassette were assembled without restricting the locking mechanisms to mimic the printing assembly. This setting gave a better understanding of the behavior of the dipsticks while exerting force (F). The type of element applied during this simulation was tetrahedral, with an element size equal to 1.43 mm. During the simulation, one side of the cassette was fixed, while the other side was the location of the applied force to the negative z-axis. The force distribution is illustrated in FIG. 47.

Example 6

Testing of the Assembled Strip

The assembled strip was added to the cassette. A solution of AuNP-S1 and AuNP-rabbit antibody at a concentration of 10 OD was mixed together at a ratio of 1:1. The solution was then used by adding 10 µl of the mixture into an Eppendorf tube, as shown in FIG. 48. Afterward, a 1 µl sample was added to the mixture and vortexed for 5 s. Here, SARS-CoV-2 Spike Protein Monoclonal Antibody (MA5-35950) was used at a concentration of 200 ug/ml as a positive sample and 1×PBS was used as a negative sample. Then, the strip was submerged into the AuNP mixture until the strip fully absorbed the solution. Finally, it was submerged into another tube that contains 1×PBS as a running buffer to wash strips from any remaining particles.

Example 7

Materials for Peptide Selection and Peptide Synthesis

MBHA Rink Amide resin, 9-Fluorenylmethoxycarbonyl (Fmoc) protected amino acids, (2-(1H-Benzotriazol-1-yl)-1,1,3,3-tetramethyluronium hexafluorophosphate (TBTU), Hydroxy benzotriazole (HOBt) were obtained from GL Biochem, China. N,N dimethylformamide (DMF), dichloromethane (DCM), N,N-diisopropylethylamine (DIPEA), piperidine, trifluoroacetic acid (TFA), triisopropylsilane (TIS), diethyl ether, acetonitrile, and formic acid were purchased from Sigma-Aldrich®.

Example 8

Peptide Design

B-cell epitopes were selected from the SARS-CoV-2 proteins based on emerging computational and experimental epitope mapping studies.[41-43,51,52] Biotin tag was incorporated into the peptide epitopes at the N-terminal site. FIG. 16 maps the synthesized peptides sequences to the spike and nucleocapsid proteins.

Example 9

Peptide Synthesis and Purification

All peptide epitopes were synthesized via a solid-phase peptide synthesis (SPPS) using a CS136X CS Biopeptide synthesizer. The peptide coupling was conducted on MBHA Rink Amide resin by agitating in a mixture of TBTU (3 eq.), HOBt (3 eq.) DIPEA (6 eq.) and Fmoc-protected amino acid (3 eq.) for an hour. Then, the resin was washed with DMF (3×), DCM (3×), and DMF (3×). 20% (v/v) piperidine/DMF was subsequently added to remove the Fmoc-protecting group from the sequence. The steps of coupling, washing and fmoc deprotection were repeated until the desired sequence was achieved. In every sequence, the last amino acid coupled was Fmoc-Lys(Biotin)-OH. The resin was then transferred out of the synthesizer and cleaved with an acidic solution of TFA:TIS:water (95:2.5:2.5). After 2 hours of mixing, the solution was collected, dispersed in cold diethyl ether, and stored at 4° C. overnight. The precipitated peptide was then centrifuged and dried in a vacuum desiccator prior to purification. The peptide purification was performed in reversed-phase prep-HPLC using the C-18 column. The purity of the synthesized peptides was calculated to be higher than 95%. A representative example of liquid chromatogram and mass spectrum of biotin-P13 is shown in FIGS. 52 and 53, respectively. In FIG. 53, MS (m/z) was calculated to be 2571.6, $[M+2H]^{2+}$ was found to be 1284.7, $[M+3H]^{3+}$ was found to be 856.7, and $[M+4H]^{4+}$ was found to be 642.9.

Example 10

Liquid Chromatography-Mass Spectroscopy (LC-MS)

The peptide purity was determined using an Agilent® 1260 Infinity LC equipped with Agilent® 6130 Quadrupole MS and Agilent® Zorbax® SB-C18 4.6×250 mm column. 0.1% (v/v) formic acid—water (A) and 0.1% (v/v) formic acid—acetonitrile (B) were chosen as the mobile phase with the flow rate of 1.5 ml/min. The chromatogram was acquired at a wavelength of 220 nm.

Example 11

Patients' Samples

Patients' serum samples were obtained from King Khalid Teaching Hospital and King Fahad Medical City in Riyadh, Saudi Arabia. This study was approved by the institutional review board committee (IRB) at both institutions and the institutional ethics and biosafety committee (IBEC) at King Abdullah University of Science and Technology (KAUST). One hundred forty-five samples were used, including 110 samples collected from PCR confirmed Covid-19 patients and 35 pre-covid samples collected and archived before November 2019 to be used as a negative control. All samples collected from Covid-19 patients tested positive for the presence of Covid-19 antibodies using a commercial antibodies test (Abbott® COVID IgG test) at King Khalid Teaching Hospital clinical laboratory. In addition, for each sample: age, gender, date of PCR testing, and date of blood sample collection were recorded.

Example 12

ELISA Protocol

Different ELISA plates and protocols were tested, the following protocol was optimized for the ELISA experiments. For peptide, streptavidin ELISA plates (Thermo Fisher®, 15120) were first washed two times with Tris washing buffer (tris buffer+0.05% Tween-20) and then coated with 60 µl peptide solution per well at a concentration of 1 µM for 90 minutes with gentle shaking; peptides were dissolved in tris washing buffer. Then the plates were washed 3 times with tris washing buffer. For S1 Spike protein (Sino Biological®, 40591-V08H), MaxiSorp ELISA plates (Thermo Fisher®, 44-2404-21) were coated with 60 µl of the protein at a concentration of 2 µg/ml and incubated overnight at 4° C.; protein was diluted in a coating buffer (carbonate-bicarbonate buffer). After the overnight incubation the plates were washed three times with tris buffer and blocked with Superblocker blocking buffer (Thermo Fisher®, Cat #37515) for 1.5 hours at room temperature. Serum samples were diluted to 1:500 in Superblocker blocking buffer, and 60 µl of the diluted samples were added to the corresponding wells; 4 replicates of each sample were added to each plate. Each sample was tested with antigen control wells in which no peptide or protein coating were done to account for the background signal. Samples were incubated for 1-hour at room temperature then the plates were washed 3 times with the washing buffer. Sixty microliters of the secondary anti-human antibodies (Abcam®, ab99759) were added to each well at a 300 ng/ml concentration and incubated at room temperature for 1-hour. Afterward, the plates were washed 3 times with washing buffer, and 60 µl of the TMB substrate (Abcam®, 171523) was added to each well and incubated for 30 minutes before adding the stop solution (Invitrogen®, SS04). Finally, plate absorbance was measured at 450 nm using an ELISA plate reader (PHERAstar®, BMGLABOTECH).

Example 13

ELISA Experiment: All Antigens Screening

ELISA was performed using streptavidin-coated plates (Thermo Fisher®, Cat #15120). Detailed ELISA protocol is provided in Example 12. Initially, experiments with single peptide coating at a concentration of 1 µM and S1 spike protein (Sino Biological®, 40591-V08H) at a concentration of 2 µg/ml were conducted in which randomly selected 18 positives and 6 negative samples were tested. The mapping of tested peptides included P4, P5, P6, P7, P10, P11, P12, P13, P14, and P15 is illustrated in FIG. 16. The sequence of the tested peptides are summarized in the above sections. Moreover, control wells with no peptide coating were performed to correct for background signal.[61] Next, peptides with the highest sensitivity and specificity were selected and tested with more patients' samples as outlined below.

Example 14

Docking Simulation

Docking between the peptides and antibodies was simulated to further elucidate the binding of the peptides to the spike and nucleocapsid regions. Three peptides based on the RBD region of the SARS-CoV-2 spike protein (P4, P5, P7) and one peptide from the nucleocapsid protein (P13) were used as targets for reported antibodies. These peptides were selected because the antibodies (7KS9 and 7CR5) reported in the literature corresponded to these regions only.[62-64] The sequence of the peptides was aligned to an appropriate antigen-antibody complex via PyMol, to obtain an initial three-dimensional conformation of the peptides (P4, P5 and P7). The conformation for P4, P5, and P7 was obtained from previously reported, RBD-directed, spike-antibody complexes.[65] All these were compared using PyMOL's alignment tool; root-mean-square deviation (RMSD) was calculated for all unbound configurations.[66] The configurations with the lowest average RMSD were chosen for docking with the antibodies. On the other hand, the initial conformation of P13 was generated from the sequence alignment of P13 and the nucleocapsid protein antibody.

Then, the docking simulations between the resultant peptide configurations and the isolated antibodies were performed according to the ClusPro protein-protein antibody docking methodology.[67-71] A negative control was developed by docking antibodies for the nucleocapsid to the spike protein-derived peptides and vice versa. The interactions were visualized and analyzed using PyMOL (v4.6.0). Next, the top 10 simulations of each docking were determined through their energy scores with Z-Score normalization and the number of interactions between the peptides and antibodies was analyzed. The only interactions between the peptide and the antibody considered in this evaluation were those pertaining to the active site of the antibody.

Example 15

ELISA Experiment: All Samples Screening

One peptide from the spike protein (P10) and one from the nucleocapsid protein (P15) were selected to be tested with all 110 positive samples and 35 negative pre-covid samples. Additionally, the sequences from P10 and P15 peptides were combined and synthesized as one longer fusion-epitopes peptide. The fusion-epitopes peptide and a mixture of the two single peptides (P10 and P15) were tested with all samples. The data from the single peptides, single peptides mixture, and fusion-epitopes peptide were compared to assess any change in the sensitivity, specificity, and accuracy.

Example 16

ELISA Data Analysis

Optical density (OD) data correction was done for all tested samples. Mean optical density (OD) signal from wells coated with a peptide was calculated and subtracted from the mean OD signal for peptide control wells, wells with no peptide coating. The corrected data from negative pre-covid samples were used to calculate the threshold value for each peptide.

Example 17

All Antigens Screening Analysis

For the peptide screening experiment, the threshold to determine positive and negative results were determined using the following formula: mean of OD signal+(3×SD).[72] Any sample with an OD result above the threshold would be considered positive, and any sample with an OD result below the threshold would be considered negative. Furthermore, sensitivity and specificity were calculated, for each peptide, using the following formulas:

$$\text{Sensitivity} = \frac{\text{true positive}}{\text{true positive} + \text{false negative}} \times 100\% \quad (1)$$

$$\text{Specifity} = \frac{\text{true negative}}{\text{true negative} + \text{false positive}} \times 100\% \quad (2)$$

$$\text{accuracy} = \frac{\text{true negative} + \text{true positive}}{\text{true negative} + \text{false positive} + \text{false negative} + \text{true negative}} \times 100\% \quad (3)$$

Example 18

All Samples Screening

OD results for all samples tested with the single, mixed, and fusion-epitopes peptides were compared using Mann-Whitney U test (Wilcoxon Rank Sum Test).

Furthermore, ROC (Receiver Operating Characteristics) curves were computed and analyzed to assess the AUC (Area Under the Curve) for each peptide.[73] Moreover, the optimal threshold was determined using Youden's J statistics[74] to determine the sensitivity, specificity, and accuracy for each peptide; 95% confidence interval was calculated with 2000 bootstrap. Statistical analysis was done with R 4.1.0.

It is intended that the invention not be limited to the particular embodiment disclosed herein contemplated for carrying out this invention, but that the invention will include all embodiments falling within the scope of the claims.

All documents, patents, journal articles and other materials cited in the present application are incorporated herein by reference.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

REFERENCES

The following references are referred to above and are incorporated herein by reference:
1. Guan W J, Ni Z Y, Hu Y, et al., 2020, Clinical Characteristics of Coronavirus Disease 2019 in China. *N. Engl. J. Med.*, 382:1708-20.
2. Chan J F, Kok K H, Zhu Z, et al., 2020, Genomic Characterization of the 2019 Novel Human-pathogenic Coronavirus Isolated from a Patient with Atypical Pneumonia after Visiting Wuhan. *Emerg Microbes Infect*, 9:221-36.
3. Huang C, Wang Y, Li X, et al., 2020, Clinical Features of Patients Infected with 2019 Novel Coronavirus in Wuhan, China. *Lancet*, 395:497-506.
4. Cucinotta D, Vanelli M, 2020, WHO Declares COVID-19 a Pandemic. *Acta Biomed*, 91:157-60.
5. Zou L, Ruan F, Huang M, et al., 2020, SARS-CoV-2 Viral Load in Upper Respiratory Specimens of Infected Patients. *N Engl J Med*, 382:1177-9.
6. To K K, Tsang O T, Leung W S, et al., 2020, Temporal Profiles of Viral Load in Posterior Oropharyngeal Saliva Samples and Serum Antibody Responses during Infection by SARSCoV-2: An Observational Cohort Study. *Lancet Infect Dis*, 20:565-74.
7. Winter A K, Hegde S T, 2020, The Important Role of Serology for COVID-19 Control. *Lancet Infect Dis*, 20:758-59.
8. Dan J M, Mateus J, Kato Y, et al., 2021, Immunological Memory to SARS-CoV-2 Assessed for up to 8 Months after Infection. *Science*, 371:eabf4063.
9. Martin J, Tena N, Asuero A G, 2021, Current State of Diagnostic, Screening and Surveillance Testing Methods for COVID-19 from an Analytical Chemistry Point of View. *Microchem J*, 167:106305.
10. Schuler C F, Gherasim C, O'Shea K, et al., 2021, Accurate Point-of-care Serology Tests for COVID-19. *PLoS One*, 16:e0248729.
11. Banerjee R, Jaiswal A, 2018, Recent Advances in Nanoparticle-based Lateral Flow Immunoassay as a Point of-care Diagnostic Tool for Infectious Agents and Diseases. *Analyst*, 143:1970-96
12. Adams E, Ainsworth M, Anand R, et al., 2020, Antibody Testing for COVID-19: A Report from the National COVID Scientific Advisory Panel. *Wellcome Open Res*, 5:139.
13. Dinnes J, Deeks J J, Berhane S, et al., 2021, Rapid, Point of-care Antigen and Molecular-based Tests for Diagnosis of SARS-CoV-2 Infection. *Cochrane Database Syst Rev*, 3:CD013705.
14. Ozbolat I T, Hospodiuk M, 2016, Current Advances and Future Perspectives in Extrusion-based Bioprinting. *Biomaterials*, 76:321-43.
15. Eckelman M J, Sherman J D, 2018, Estimated Global Disease Burden From U S Health Care Sector Greenhouse Gas Emissions. *Am J Public Health*, 108:S120-2.
16. Leiden A, Cerdas F, Noriega D, et al., 2020, Life Cycle Assessment of a Disposable and a Reusable Surgery Instrument Set for Spinal Fusion Surgeries. *Resour Conserv Recycl*, 156:104704.
17. Unger S R, Hottle T A, Hobbs S R, et al., 2017, Do Singleuse Medical Devices Containing Biopolymers Reduce the Environmental Impacts of Surgical Procedures Compared with their Plastic Equivalents? *J Health Serv Res Policy*, 22:218-25.
18. Gebhardt A, 2011, Understanding Additive Manufacturing. In: Understanding Additive Manufacturing. Hanser Pub Inc., Cincinnati, OH
19. Joshi S C, Sheikh A A, 2015, 3D Printing in Aerospace and its Long-term Sustainability. *Virtual Phys Prototyp*, 10:175-85.
20. Ng W L, Chua C K, Shen Y F, 2019, Print Me An Organ! Why We Are Not There Yet. *Prog Polym Sci*, 97:101145.
21. Pant A, Lee A Y, Karyappa R, et al., 2021, 3D Food Printing of Fresh Vegetables Using Food Hydrocolloids for Dysphagic Patients. *Food Hydrocolloids*, 114:106546.
22. Choong Y Y, Tan H W, Patel D C, et al., 2020, The Global Rise of 3D Printing during the COVID-19 Pandemic. *Nat Rev Mater*, 5:637-9.
23. Harvey W T, Carabelli A M, Jackson B, et al., 2021, SARSCoV-2 Variants, Spike Mutations and Immune Escape. *Nat Rev Microbiol*, 19:409-24.
24. World Health Organization, 2021, Tracking SARS-CoV-2 Variants, World Health Organization, Geneva. [Last accessed on 2021 Jul. 25].
25. Jazayeri M H, Amani H, Pourfatollah A A, et al., 2016, Enhanced Detection Sensitivity of Prostate-specific Antigen via PSA-Conjugated Gold Nanoparticles Based on Localized Surface Plasmon Resonance: GNP-coated Anti-PSA/LSPR as a Novel Approach for the Identification of Prostate Anomalies. *Cancer Gene Ther,* 23:365-9.
26. Pollitt M J, Buckton G, Piper R, et al., 2015, Measuring Antibody Coatings on Gold Nanoparticles by Optical Spectroscopy. *RSC Adv,* 5:24521-7.
27. Yetisen A K, Akram M S, Lowe C R, 2013, Paper-based Microfluidic Point-of-care Diagnostic Devices. *Lab Chip,* 13:2210-51.
28. Stansbury J W, Idacavage M J, 2016, 3D Printing with Polymers: Challenges among Expanding Options and Opportunities. *Dent Mater,* 32:54-64.
29. Infuehr R, Pucher N, Heller C, et al., 2007, Functional Polymers by Two-photon 3D Lithography. *Appl Surface Sci,* 254:836-40.
30. Milovanović A, Milošević M, Mladenović G, et al., 2019, Experimental Dimensional Accuracy Analysis of Reformer Prototype Model Produced by FDM and SLA 3D Printing Technology. *Springer International Publishing, Cham, p*84-95.
31. Gibson I, Rosen D, Stucker B, et al., 2021, Material Extrusion. In: Additive Manufacturing Technologies. Springer International Publishing, Cham, p171-201.
32. Kun K, 2016, Reconstruction and Development of a 3D Printer Using FDM Technology. *Proc Eng,* 149:203-211.
33. Gibson I, Rosen D, Stucker B, 2015, Vat Photopolymerization Processes. In: Additive Manufacturing Technologies: 3*D Printing, Rapid Prototyping, and Direct Digital Manufacturing. Springer New York, p*63-106.
34. Cui, J.; Li, F.; Shi, Z. L., Origin and Evolution of Pathogenic Coronaviruses. *Nat. Rev. Microbiol.* 2019, 17 (3), 181-192.
35. Venter, M.; Richter, K., Towards Effective Diagnostic Assays for Covid-19: A Review. *J. Clin. Pathol.* 2020, 73 (7), 370-377.
36. Deeks, J. J.; Dinnes, J.; Takwoingi, Y.; Davenport, C.; Spijker, R.; Taylor-Phillips, S.; Adriano, A.; Beese, S.; Dretzke, J.; Ferrante di Ruffano, L.; Harris, I. M.; Price, M. J.; Dittrich, S.; Emperador, D.; Hooft, L.; Leeflang, M. M.; Van den Bruel, A., Antibody Tests for Identification of Current and Past Infection with Sars-Cov-2. *Cochrane Database Syst. Rev.* 2020, 6 (6), Cd013652.
37. Kohl, T. O.; Ascoli, C. A., Indirect Immunometric Elisa. *Cold Spring Harb Protoc.* 2017, 2017 (5).
38. Mishra, A. R.; Hutke, V. R.; Satav, A. R.; Ali, S. A.; Daginawala, H. F.; Singh, L. R.; Kashyap, R. S., Synthetic Peptides Are Better Than Native Antigens for Development of Elisa Assay for Diagnosis of Tuberculosis. *Int. J. Pept. Res. Ther.* 2017, 23 (2), 247-257.
39. Petherick, A., Developing Antibody Tests for Sars-Cov-2. *Lancet.* 2020, 395 (10230), 1101-1102.
40. Groß, A.; Hashimoto, C.; Sticht, H.; Eichler, J., Synthetic Peptides as Protein Mimics. *Front. Bioeng. Biotechnol.* 2016, 3 (211).
41. Poh, C. M.; Carissimo, G.; Wang, B.; Amrun, S. N.; Lee, C. Y.; Chee, R. S.; Fong, S. W.; Yeo, N. K.; Lee, W. H.; Torres-Ruesta, A.; Leo, Y. S.; Chen, M. I.; Tan, S. Y.; Chai, L. Y. A.; Kalimuddin, S.; Kheng, S. S. G.; Thien, S. Y.; Young, B. E.; Lye, D. C.; Hanson, B. J.; Wang, C. I.; Renia, L.; Ng, L. F. P., Two Linear Epitopes on the Sars-Cov-2 Spike Protein That Elicit Neutralising Antibodies in Covid-19 Patients. *Nat Commun.* 2020, 11 (1), 2806.
42. Alves, D.; Curvello, R.; Henderson, E.; Kesarwani, V.; Walker, J. A.; Leguizamon, S. C.; McLiesh, H.; Raghuwanshi, V. S.; Samadian, H.; Wood, E. M.; McQuilten, Z. K.; Graham, M.; Wieringa, M.; Korman, T. M.; Scott, T. F.; Banaszak Holl, M. M.; Garnier, G.; Corrie, S. R., Rapid Gel Card Agglutination Assays for Serological Analysis Following Sars-Cov-2 Infection in Humans. *ACS Sensors.* 2020, 5 (8), 2596-2603.
43. Amrun, S. N.; Lee, C. Y.; Lee, B.; Fong, S. W.; Young, B. E.; Chee, R. S.; Yeo, N. K.; Torres-Ruesta, A.; Carissimo, G.; Poh, C. M.; Chang, Z. W.; Tay, M. Z.; Chan, Y. H.; Chen, M. I.; Low, J. G.; Tambyah, P. A.; Kalimuddin, S.; Pada, S.; Tan, S. Y.; Sun, L. J.; Leo, Y. S.; Lye, D. C.; Renia, L.; Ng, L. F. P., Linear B-Cell Epitopes in the Spike and Nucleocapsid Proteins as Markers of Sars-Cov-2 Exposure and Disease Severity. *EBioMedicine.* 2020, 58, 102911.
44. Farrera-Soler, L.; Daguer, J. P.; Barluenga, S.; Vadas, O.; Cohen, P.; Pagano, S.; Yerly, S.; Kaiser, L.; Vuilleumier, N.; Winssinger, N., Identification of Immunodominant Linear Epitopes from Sars-Cov-2 Patient Plasma. *PLoS One.* 2020, 15 (9), e0238089.
45. Li, Y.; Lai, D. Y.; Lei, Q.; Xu, Z. W.; Wang, F.; Hou, H.; Chen, L.; Wu, J.; Ren, Y.; Ma, M. L.; Zhang, B.; Chen, H.; Yu, C.; Xue, J. B.; Zheng, Y. X.; Wang, X. N.; Jiang, H. W.; Zhang, H. N.; Qi, H.; Guo, S. J.; Zhang, Y.; Lin, X.; Yao, Z.; Pang, P.; Shi, D.; Wang, W.; Yang, X.; Zhou, J.; Sheng, H.; Sun, Z.; Shan, H.; Fan, X.; Tao, S. C., Systematic Evaluation of Igg Responses to Sars-Cov-2 Spike Protein-Derived Peptides for Monitoring Covid-19 Patients. Cell. *Mol. Immunol.* 2021, 18 (3), 621-631.
46. Polvere, I.; Voccola, S.; Cardinale, G.; Fumi, M.; Aquila, F.; Parrella, A.; Madera, J. R.; Stilo, R.; Vito, P.; Zotti, T., A Peptide-Based Assay Discriminates Individual Antibody Response to Sars-Cov-2. *Genes Dis.* 2021.
47. Simula, E. R.; Manca, M. A.; Jasemi, S.; Uzzau, S.; Rubino, S.; Manchia, P.; Bitti, A.; Palermo, M.; Sechi, L. A., Hcov-N163 and Sars-Cov-2 Share Recognized Epitopes by the Humoral Response in Sera of People Collected Pre- and During Cov-2 Pandemic. *Microorganisms.* 2020, 8 (12).
48. Li, Y.; Lai, D.-y.; Zhang, H.-n.; Jiang, H.-w.; Tian, X.; Ma, M.-l.; Qi, H.; Meng, Q.-f.; Guo, S.-j.; Wu, Y.; Wang, W.; Yang, X.; Shi, D.-w.; Dai, J.-b.; Ying, T.; Zhou, J.; Tao, S.-c., Linear Epitopes of Sars-Cov-2 Spike Protein Elicit Neutralizing Antibodies in Covid-19 Patients. Cell. *Mol. Immunol.* 2020, 17 (10), 1095-1097.
49. Ernst, E.; Wolfe, P.; Stahura, C.; Edwards, K. A., Technical Considerations to Development of Serological Tests for Sars-Cov-2. *Talanta.* 2021, 224, 121883-121883.
50. Ayouba, A.; Touré, A.; Butel, C.; Keita, A. K.; Binetruy, F.; Sow, M. S.; Foulongne, V.; Delaporte, E.; Peeters, M., Development of a Sensitive and Specific Serological Assay Based on Luminex Technology for Detection of Antibodies to Zaire Ebola Virus. *J. Clin. Microbiol.* 2017, 55 (1), 165-176.
51. Shrock, E.; Fujimura, E.; Kula, T.; Timms, R. T.; Lee, I. H.; Leng, Y.; Robinson, M. L.; Sie, B. M.; Li, M. Z.; Chen, Y.; Logue, J.; Zuiani, A.; McCulloch, D.; Lelis, F. J. N.; Henson, S.; Monaco, D. R.; Travers, M.; Habibi, S.; Clarke, W. A.; Caturegli, P.; Laeyendecker, O.; Piechocka-Trocha, A.; Li, J. Z.; Khatri, A.; Chu, H. Y.; Villani, A. C.; Kays, K.; Goldberg, M. B.; Hacohen, N.; Filbin, M. R.; Yu, X. G.; Walker, B. D.; Wesemann, D. R.; Larman, H. B.; Lederer, J. A.; Elledge, S. J., Viral Epitope Profiling of Covid-19 Patients Reveals Cross-Reactivity and Correlates of Severity. *Science.* 2020, 370 (6520).
52. Grifoni, A.; Sidney, J.; Zhang, Y.; Scheuermann, R. H.; Peters, B.; Sette, A., A Sequence Homology and Bioin- 53. Zhang, B.-z.; Hu, Y.-f.; Chen, L.-l.; Yau, T.; Tong, Y.-g.; Hu, J.-c.; Cai, J.-p.; Chan, K.-H.; Dou, Y.; Deng, J.; Wang, X.-l.; Hung, I. F.-N.; To, K. K.-W.; Yuen, K. Y.; Huang, J.-D., Mining of Epitopes on Spike Protein of Sars-Cov-2 from Covid-19 Patients. *Cell Res.* 2020, 30 (8), 702-704.

54. Ahmed, S. F.; Quadeer, A. A.; McKay, M. R., Covidep: A Web-Based Platform for Real-Time Reporting of Vaccine Target Recommendations for Sars-Cov-2. *Nat. Protoc.* 2020, 15 (7), 2141-2142.

55. Grossberg, A. N.; Koza, L. A.; Ledreux, A.; Prusmack, C.; Krishnamurthy, H. K.; Jayaraman, V.; Granholm, A.-C.; Linseman, D. A., A Multiplex Chemiluminescent Immunoassay for Serological Profiling of Covid-19-Positive Symptomatic and Asymptomatic Patients. *Nat Commun.* 2021, 12 (1), 740.

56. Diener, C.; Garza Ramos Martinez, G.; Moreno Blas, D.; Castillo González, D. A.; Corzo, G.; Castro-Obregon, S.; Del Rio, G., Effective Design of Multifunctional Peptides by Combining Compatible Functions. *PLoS Comput. Biol.* 2016, 12 (4), e1004786-e1004786.

57. Hodcroft, E. Overview of Variants/Mutations.

58. Cai, X.-f.; Chen, J.; li Hu, J.-.; Long, Q.-x.; Deng, H.-j.; Liu, P.; Fan, K.; Liao, P.; Liu, B.-z.; Wu, G.-c.; Chen, Y.-k.; Li, Z.-j.; Wang, K.; Zhang, X.-l.; Tian, W.-g.; Xiang, J.-l.; Du, H.-x.; Wang, J.; Hu, Y.; Tang, N.; Lin, Y.; Ren, J.-h.; Huang, L.-y.; Wei, J.; Gan, C.-y.; Chen, Y.-m.; Gao, Q.-z.; Chen, A.-m.; He, C.-l.; Wang, D.-X.; Hu, P.; Zhou, F.-C.; Huang, A.-l.; Wang, D.-q., A Peptide-Based Magnetic Chemiluminescence Enzyme Immunoassay for Serological Diagnosis of Coronavirus Disease 2019. *J Infect Dis.* 2020, 222 (2), 189-193.

59. Chen, Z.; Zhang, Z.; Zhai, X.; Li, Y.; Lin, L.; Zhao, H.; Bian, L.; Li, P.; Yu, L.; Wu, Y.; Lin, G., Rapid and Sensitive Detection of Anti-Sars-Cov-2 Igg, Using Lanthanide-Doped Nanoparticles-Based Lateral Flow Immunoassay. *Anal. Chem.* 2020, 92 (10), 7226-7231.

60. Lew, T. T. S.; Aung, K. M. M.; Ow, S. Y.; Amrun, S. N.; Sutarlie, L.; Ng, L. F. P.; Su, X., Epitope-Functionalized Gold Nanoparticles for Rapid and Selective Detection of Sars-Cov-2 Igg Antibodies. *ACS Nano.* 2021, 15 (7), 12286-12297.

61. Haberland, A.; Müller, J.; Wallukat, G.; Wenzel, K., Antigen-Free Control Wells in an Elisa Set-up for the Determination of Autoantibodies against G Protein-Coupled Receptors-a Requisite for Correct Data Evaluation. *Anal. Bioanal. Chem.* 2018, 410 (21), 5101-5105.

62. Banach, B. B.; Cerutti, G.; Fahad, A. S.; Shen, C.-H.; de Souza, M. O.; Katsamba, P. S.; Tsybovsky, Y.; Wang, P.; Nair, M. S.; Huang, Y.; Urdiniz, I. M. F.; Steiner, P. J.; Gutiérrez-González, M.; Liu, L.; López Acevedo, S. N.; Nazzari, A.; Wolfe, J. R.; Luo, Y.; Olia, A. S.; Teng, I.-T.; Yu, J.; Zhou, T.; Reddem, E. R.; Bimela, J.; Pan, X.; Madan, B.; Laflin, A. D.; Nimrania, R.; Yuen, K.-T.; Whitehead, T. A.; Ho, D. D.; Kwong, P. D.; Shapiro, L.; DeKosky, B. J., Paired Heavy and Light Chain Signatures Contribute to Potent Sars-Cov-2 Neutralization in Public Antibody Responses. *bioRxiv.* 2021, 2020.12.31.424987.

63. Ju, B.; Zhang, Q.; Ge, J.; Wang, R.; Sun, J.; Ge, X.; Yu, J.; Shan, S.; Zhou, B.; Song, S.; Tang, X.; Yu, J.; Lan, J.; Yuan, J.; Wang, H.; Zhao, J.; Zhang, S.; Wang, Y.; Shi, X.; Liu, L.; Zhao, J.; Wang, X.; Zhang, Z.; Zhang, L., Human Neutralizing Antibodies Elicited by Sars-Cov-2 Infection. *Nature.* 2020, 584 (7819), 115-119.

64. Kang, S.; Yang, M.; He, S.; Wang, Y.; Chen, X.; Chen, Y.-Q.; Hong, Z.; Liu, J.; Jiang, G.; Chen, Q.; Zhou, Z.; Zhou, Z.; Huang, Z.; Huang, X.; He, H.; Zheng, W.; Liao, H.-X.; Xiao, F.; Shan, H.; Chen, S., A Sars-Cov-2 Antibody Curbs Viral Nucleocapsid Protein-Induced Complement Hyperactivation. *Nat Commun.* 2021, 12 (1), 2697.

65. Burley, S. K.; Bhikadiya, C.; Bi, C.; Bittrich, S.; Chen, L.; Crichlow, G. V.; Christie, C. H.; Dalenberg, K.; Di Costanzo, L.; Duarte, J. M.; Dutta, S.; Feng, Z.; Ganesan, S.; Goodsell, D. S.; Ghosh, S.; Green, R. K.; Guranović, V.; Guzenko, D.; Hudson, B. P.; Lawson, Catherine L.; Liang, Y.; Lowe, R.; Namkoong, H.; Peisach, E.; Persikova, I.; Randle, C.; Rose, A.; Rose, Y.; Sali, A.; Segura, J.; Sekharan, M.; Shao, C.; Tao, Y.-P.; Voigt, M.; Westbrook, John D.; Young, J. Y.; Zardecki, C.; Zhuravleva, M., Rcsb Protein Data Bank: Powerful New Tools for Exploring 3d Structures of Biological Macromolecules for Basic and Applied Research and Education in Fundamental Biology, Biomedicine, Biotechnology, Bioengineering and Energy Sciences. *Nucleic Acids Res.* 2020, 49 (D1), D437-D451.

66. Norel, R.; Petrey, D.; Wolfson, H. J.; Nussinov, R., Examination of Shape Complementarity in Docking of Unbound Proteins. *Proteins: Structure, Function, and Bioinformatics.* 1999, 36 (3), 307-317.

67. Brenke, R.; Hall, D. R.; Chuang, G. Y.; Comeau, S. R.; Bohnuud, T.; Beglov, D.; Schueler-Furman, O.; Vajda, S.; Kozakov, D., Application of Asymmetric Statistical Potentials to Antibody-Protein Docking. *Bioinformatics.* 2012, 28 (20), 2608-14.

68. Desta, I. T.; Porter, K. A.; Xia, B.; Kozakov, D.; Vajda, S., Performance and Its Limits in Rigid Body Protein-Protein Docking. *Structure.* 2020, 28 (9), 1071-1081.e3.

69. Kozakov, D.; Beglov, D.; Bohnuud, T.; Mottarella, S. E.; Xia, B.; Hall, D. R.; Vajda, S., How Good Is Automated Protein Docking? *Proteins.* 2013, 81 (12), 2159-66.

70. Kozakov, D.; Hall, D. R.; Xia, B.; Porter, K. A.; Padhorny, D.; Yueh, C.; Beglov, D.; Vajda, S., The Cluspro Web Server for Protein-Protein Docking. *Nat. Protoc.* 2017, 12 (2), 255-278.

71. Vajda, S.; Yueh, C.; Beglov, D.; Bohnuud, T.; Mottarella, S. E.; Xia, B.; Hall, D. R.; Kozakov, D., New Additions to the Cluspro Server Motivated by Capri. *Proteins.* 2017, 85 (3), 435-444.

72. Gonzalez-Moa, M. J.; Van Dorst, B.; Lagatie, O.; Verheyen, A.; Stuyver, L.; Biamonte, M. A., Proof-of-Concept Rapid Diagnostic Test for Onchocerciasis: Exploring Peptide Biomarkers and the Use of Gold Nanoshells as Reporter Nanoparticles. *ACS Infect Dis.* 2018, 4 (6), 912-917.

73. Robin, X.; Turck, N.; Hainard, A.; Tiberti, N.; Lisacek, F.; Sanchez, J.-C.; Müller, M., Proc: An Open-Source Package for R and S+ to Analyze and Compare Roc Curves. *BMC Bioinformatics.* 2011, 12 (1), 77.

74. Youden, W. J., Index for Rating Diagnostic Tests. *Cancer.* 1950, 3 (1), 32-35.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, products specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

While the present disclosure has been disclosed with references to certain embodiments, numerous modifications, alterations, and changes to the described embodiments are possible without departing from the sphere and scope of the present disclosure, as defined in the appended claims. Accordingly, it is intended that the present disclosure is not limited to the described embodiments, but that it has the full scope defined by the language of the following claims, and equivalents thereof.

What is claimed is:

1. A method of fabricating a lateral flow immunoassay (LFIA) comprising:

synthesizing and screening at least one peptide antigen;
conjugating the peptide antigen with at least one tag;
printing a test strip;
determining the minimum thickness of a test cassette; and
assembling the LFIA,
wherein the peptide antigen binds specifically to at least one analyst,
wherein at least one control line and at least one test line are printed on the test strip, and wherein the material in the test line binds the complex formed by the analyst and the peptide antigen conjugated with the tag, wherein the epitopes are at least one selected from the group consisting of peptides with amino acid sequences provided in SEQ ID Nos. 1-10 and 10-19.

2. The method of claim 1, wherein the at least one peptide antigen is at least one fusion-epitopes peptide.

3. The method of claim 2, wherein the epitopes are whole or part of at least one antigenic protein of Acute Respiratory Syndrome Corona Virus 2 (SARS-CoV-2).

4. The method of claim 2, wherein the at least one fusion-epitopes peptide is obtained by fusing the peptide provided in SEQ ID No. 5 and at least one peptide provided in the group consisting SEQ ID Nos. 10, 13 and 19 or by fusing the peptide provided in SEQ ID No. 7 and the peptide provided in SEQ ID No. 8.

5. The method of claim 2, wherein the at least one fusion-epitopes peptide is provided in SEQ ID No. 11.

6. The method of claim 1, wherein the at least one analyst is at least one antibody.

7. The method of claim 1, wherein the at least one analyst is at least one anti-SARS-CoV-2 antibody.

8. The method of claim 1, wherein the minimum thickness of the test cassette is determined by a finite element analysis (FEA) simulation.

9. The method of claim 1, wherein the test cassette with the minimum thickness uses the least amount of materials to fabricate, when the cassettes does not break under handling forces of 5 N.

10. The method of claim 1, wherein the test cassette is printed.

11. The method of claim 1, wherein the at least one tag is at least one selected from the group consisting of colored nano-particle, silver nano-particle, carbon nano-particle, magnetic nano-particle, or quantum dot.

12. The method of claim 1, wherein the at least one tag is at least one selected from a gold nano-particle (AuNP) or a iron oxide nano-particle ($Fe_2O_3$).

13. The method of claim 1, further comprising:

adding at least one agent binds to the control line but not the test line to the at least one tag conjugated peptide antigen.

14. The method of claim 1, wherein the at least one peptide antigen detects the at least one analyst with sensitivity of at least 85%, a specificity of at least 95%, and an accuracy of at least 85%.

15. The method of claim 1, wherein the at least one peptide antigen has at least 20 interactions with the at least one analyst and is determined using docking simulation.

16. A fusion-peptide for immunoassay comprising at least two epitopes of SARS-CoV-2, wherein the epitopes are linked by peptide bond, wherein the epitopes are at least one selected from the group consisting of peptides with amino acid sequences provided in SEQ ID Nos. 1-10 and 10-19.

17. The fusion-peptide of claim 16, wherein the epitopes are different.

18. The fusion-peptide as in claim 16, wherein the fusion-epitopes peptide is obtained by fusing the peptide provided in SEQ ID No. 5 and at least one peptide provided in the group consisting SEQ ID Nos. 10, 13 and 19 or by fusing the peptide provided in SEQ ID No. 7 and the peptide provided in SEQ ID No. 8.

19. The fusion-peptide as in claim 16, wherein the fusion-epitopes peptide is provided in SEQ ID No. 11.

* * * * *